United States Patent
Momoki

(10) Patent No.: US 12,406,755 B2
(45) Date of Patent: Sep. 2, 2025

(54) DOCUMENT CREATION SUPPORT APPARATUS, METHOD, AND PROGRAM

(71) Applicant: FUJIFILM Corporation, Tokyo (JP)

(72) Inventor: Yohei Momoki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 320 days.

(21) Appl. No.: 17/942,166

(22) Filed: Sep. 11, 2022

(65) Prior Publication Data
US 2023/0005580 A1 Jan. 5, 2023

Related U.S. Application Data

(63) Continuation of application No. PCT/JP2021/010610, filed on Mar. 16, 2021.

(30) Foreign Application Priority Data

Mar. 17, 2020 (JP) .................. 2020-046019

(51) Int. Cl.
*G16H 15/00* (2018.01)
*G06T 7/00* (2017.01)
*G06T 7/11* (2017.01)
*G16H 30/40* (2018.01)

(52) U.S. Cl.
CPC ........... *G16H 15/00* (2018.01); *G06T 7/0012* (2013.01); *G06T 7/11* (2017.01); *G16H 30/40* (2018.01); *G06T 2207/20081* (2013.01)

(58) Field of Classification Search
CPC .......... G16H 15/00; G16H 30/40; G06T 7/11; G06T 7/0012
See application file for complete search history.

(56) References Cited

U.S. PATENT DOCUMENTS

2007/0244393 A1* 10/2007 Oshiki .................. G06T 7/0012
  600/463
2009/0076853 A1 3/2009 Sagawa
(Continued)

FOREIGN PATENT DOCUMENTS

| CN | 110111864 A | * 8/2019 | ........... G06N 3/0445 |
| JP | 2008200373 | 9/2008 | |

(Continued)

OTHER PUBLICATIONS

"Office Action of Japan Counterpart Application", issued on Sep. 5, 2023, with English translation thereof, p. 1-p. 5.
(Continued)

*Primary Examiner* — David Bilodeau
(74) *Attorney, Agent, or Firm* — JCIPRNET

(57) ABSTRACT

A document creation support apparatus includes at least one processor, and the processor specifies, with respect to a first region specified in a first image of a subject, a second region corresponding to the first region in each of a plurality of second images of the subject whose imaging time is different from that of the first image. The processor specifies a second description regarding the specified second region, which is included in a plurality of sentences related to each of the plurality of second images. The processor displays a plurality of second descriptions specified for each of the plurality of second images in a switchable manner.

10 Claims, 19 Drawing Sheets

(56) References Cited

U.S. PATENT DOCUMENTS

| | | | |
|---|---|---|---|
| 2011/0002515 A1* | 1/2011 | Futami | G16H 15/00 |
| | | | 382/128 |
| 2012/0183188 A1 | 7/2012 | Moriya | |
| 2015/0146947 A1* | 5/2015 | Matsumoto | G06F 18/24 |
| | | | 382/128 |
| 2017/0243348 A1* | 8/2017 | Sakamoto | A61B 6/469 |
| 2017/0301092 A1 | 10/2017 | Kikuchi | |
| 2018/0235563 A1* | 8/2018 | Nam | A61B 8/5238 |
| 2019/0267132 A1* | 8/2019 | Fuchigami | G06T 11/60 |
| 2019/0279408 A1* | 9/2019 | Hirakawa | G06V 30/416 |
| 2019/0279751 A1 | 9/2019 | Nakamura et al. | |
| 2021/0035676 A1 | 2/2021 | Nakamura et al. | |

FOREIGN PATENT DOCUMENTS

| | | |
|---|---|---|
| JP | 2009070201 | 4/2009 |
| JP | 2011024622 | 2/2011 |
| JP | 2016057695 | 4/2016 |
| JP | 2017189390 | 10/2017 |
| JP | 2017204041 | 11/2017 |
| JP | 2019153249 | 9/2019 |
| JP | 2019153250 | 9/2019 |
| WO | 2011033769 | 3/2011 |
| WO | 2016035312 | 3/2016 |
| WO | 2019208130 | 10/2019 |

OTHER PUBLICATIONS

"International Search Report (Form PCT/ISA/210) of PCT/JP2021/010610," mailed on May 11, 2021, with English translation thereof, pp. 1-6.

"Written Opinion of the International Searching Authority (Form PCT/ISA/237)" of PCT/JP2021/010610, mailed on May 11, 2021, with English translation thereof, pp. 1-8.

* cited by examiner

FIG. 4
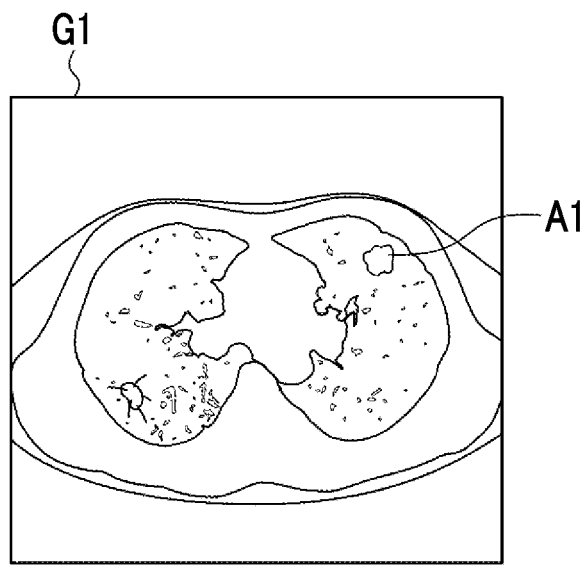
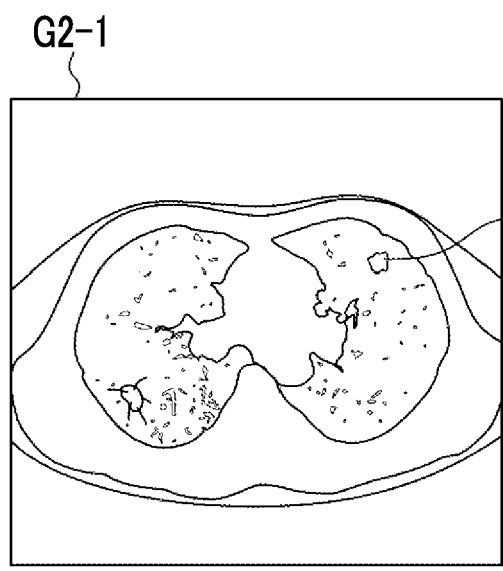
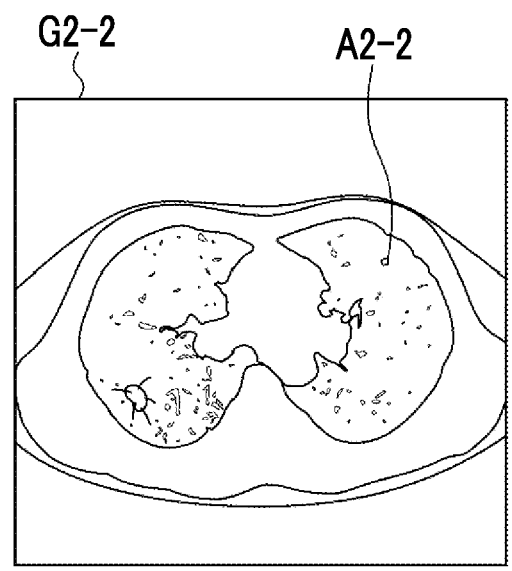

FIG. 5

```
LOCATION OF ABNORMAL SHADOW: UNDER LEFT LUNG PLEURA
SIZE OF ABNORMAL SHADOW: 4.2 cm IN DIAMETER
SHAPE OF BOUNDARY: IRREGULAR
ABSORPTION VALUE: SOLID
SPICULA: +
TUMOR
PLEURAL CONTACT: +
PLEURAL INVAGINATION: +
PLEURAL INFILTRATION: -
CAVITY:   -
CALCIFICATION: -
```
30

```
15 mm-SIZED NODULE ON PERIPHERY
OF LEFT UPPER LOBE S1+2b SHOWS NO SIGNIFICANT CHANGES IN SIZE OR PROPERTIES.
THERE IS NO CHANGE EVEN IF IT GOES BACK TO 2/3/2016.
SHADOW OF TUMOR OF RIGHT LUNG S6 IS ABOUT 6.5 × 4 cm AND IS INCREASING.
CAVITY IN CENTER OF TUMOR IS ALSO LARGER THAN LAST TIME.
TUMOR IN MIDDLE LOBE OF RIGHT LUNG IS INCREASING.
NO OBVIOUS LUNG METASTASES ARE FOUND.
```

TUMOR, WITH CAVITY — 31

D2-1

```
SHADOW OF TUMOR OF RIGHT LUNG S6 IS ABOUT 6.5 × 4 cm AND IS INCREASING.
CAVITY IN CENTER OF TUMOR IS ALSO LARGER THAN LAST TIME.
```

DOCUMENT CREATION SUPPORT APPARATUS, METHOD, AND PROGRAM

CROSS REFERENCE TO RELATED APPLICATIONS

The present application is a Continuation of PCT International Application No. PCT/JP2021/10610, filed on Mar. 16, 2021, which claims priority to Japanese Patent Application No. 2020-046019, filed on Mar. 17, 2020. Each application above is hereby expressly incorporated by reference, in its entirety, into the present application.

BACKGROUND

Technical Field

The present disclosure relates to a document creation support apparatus, method, and program.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be specified and analyzed accurately by image diagnosis using CT images, MRI images, and the like, appropriate treatment can be performed.

In addition, image diagnosis is also made by analyzing a medical image via computer-aided diagnosis (CAD) using a learning model in which machine learning is performed by deep learning or the like, discriminating properties such as the shape, density, position, and size of structures of interest such as abnormal shadows included in the medical images, and acquiring them as an analysis result. The analysis result acquired by CAD is associated with examination information such as a patient name, gender, age, and a modality that has acquired the medical image, and is saved in a database. The medical image and the analysis result are transmitted to a terminal of a radiologist who interprets the medical images. The radiologist interprets the medical image by referring to the transmitted medical image and analysis result and creates an interpretation report, in his or her own terminal.

Meanwhile, with the improvement of the performance of the CT apparatus and the MRI apparatus described above, the number of medical images to be interpreted is also increasing. However, since the number of radiologists has not kept up with the number of medical images, it is desired to reduce the burden of the image interpretation work of the radiologists. Therefore, various methods have been proposed to support the creation of medical documents such as interpretation reports. For example, JP2019-153250A proposes a method for automatically generating a sentence to be included in an interpretation report based on keywords input by a radiologist and on information indicating a property of a structure of interest (hereinafter referred to as property information) included in an analysis result of a medical image. In the methods described in JP2019-153250A, a sentence relating to medical care (hereinafter referred to as a medical sentence) is created by using a learning model in which machine learning is performed, such as a recurrent neural network trained to generate a sentence from characters representing the input property information. By automatically generating the medical sentence as in the method described in JP2019-153250A, it is possible to reduce a burden on a radiologist at the time of creating a medical document such as an interpretation report.

Incidentally, in the case of following up on a patient, in creating an interpretation report based on the latest medical image of the patient, the past medical image interpretation report is often referred to. In order to easily refer to such a past interpretation report, a method has been proposed in which a past image of the same patient is specified and findings information associated with the past image is acquired (see JP2017-204041A). In addition, a method has been proposed in which, in a case where there is a past image of the same part for the same patient, the current image and the past image of the part are displayed at the same time, and in a case where there is findings information about the region, the findings information is transmitted (see JP2011-024622A). Further, a method has been proposed in which an interpretation report for a current medical image and an interpretation report for a past medical image are displayed at the same time (see JP2017-189390A).

In creating an interpretation report that describes the findings about abnormal shadows included in a medical image of a certain patient, there may be a plurality of sentences such as interpretation reports that describe past images of the same patient and corresponding findings. In such a case, if the sentence such as the interpretation report for the past image can be referred to, the interpretation report including the findings about the abnormal shadow included in the current medical image can be efficiently created.

SUMMARY OF THE INVENTION

The present disclosure has been made in view of the above circumstances, and an object thereof is to enable efficient reference to sentences about images in a case where there are a plurality of images with different imaging times.

According to an aspect of the present disclosure, there is provided a document creation support apparatus comprising at least one processor, in which the processor is configured to specify, with respect to a first region specified in a first image of a subject, a second region corresponding to the first region in each of a plurality of second images of the subject whose imaging time is different from that of the first image, specify a second description regarding the specified second region, which is included in a plurality of sentences related to each of the plurality of second images, and display a plurality of second descriptions specified for each of the plurality of second images in a switchable manner.

In the document creation support apparatus according to the aspect of the present disclosure, the processor may be configured to further display a description region for describing a sentence related to the first region.

In the document creation support apparatus according to the aspect of the present disclosure, the processor may be configured to transcribe at least one of the plurality of second descriptions to the description region.

In the document creation support apparatus according to the aspect of the present disclosure, the processor may be configured to analyze the first region to generate a first description regarding the first region, and display the first description in the description region.

In the document creation support apparatus according to the aspect of the present disclosure, the processor may be configured to derive a difference between a property related to the first region included in the first description and a property related to the second region included in the second description specified for each of the plurality of second images, and display the difference between the property included in the first description and the property included in the second description in a visually recognizable manner.

In the document creation support apparatus according to the aspect of the present disclosure, the processor may be configured to derive a difference between the first region and the second region.

In the document creation support apparatus according to the aspect of the present disclosure, the processor may be configured to display the second description in a case where the difference has been derived.

In the document creation support apparatus according to the aspect of the present disclosure, the processor may be configured to notify that the difference has not been derived in a case where the difference has not been derived.

According to another aspect of the present disclosure, there is provided a document creation support method comprising: specifying, with respect to a first region specified in a first image of a subject, a second region corresponding to the first region in each of a plurality of second images of the subject whose imaging time is different from that of the first image; specifying a second description regarding the specified second region, which is included in a plurality of sentences related to each of the plurality of second images; and displaying a plurality of second descriptions specified for each of the plurality of second images in a switchable manner.

In addition, a program for causing a computer to execute the document creation support method according to the aspect of the present disclosure may be provided.

According to the aspects of the present disclosure, in a case where there are a plurality of images with different imaging times, the sentence about the images can be efficiently referred to.

BRIEF DESCRIPTION OF THE DRAWINGS

FIG. 4 is a diagram showing a first medical image and a second medical image.

FIG. 5 is a diagram for describing an example of property information.

FIG. 6 is a diagram for describing the specification of a second description.

DETAILED DESCRIPTION OF THE PREFERRED EMBODIMENTS

Figure 1:
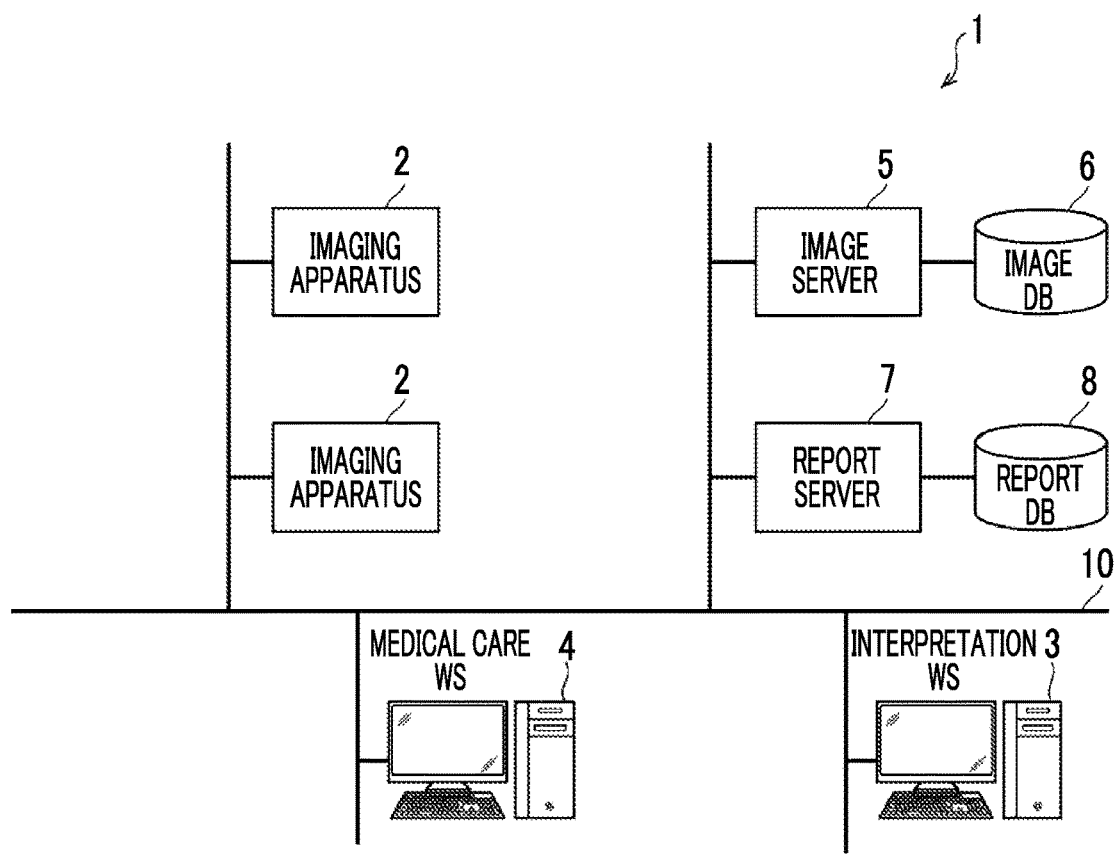
FIG. 1 is a diagram showing a schematic configuration of a medical information system to which a document creation support apparatus according to a first embodiment of the present disclosure is applied.

Hereinafter, embodiments of the present disclosure will be described with reference to the drawings. First, a configuration of a medical information system 1 to which a document creation support apparatus according to the present embodiment is applied will be described. FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, and a report database (hereinafter referred to as a report DB) 8 are communicably connected to each other through a wired or wireless network 10.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded to and installed on the computer in response to a request.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of a radiology department to interpret a medical image and to create an interpretation report, and encompasses a document creation support apparatus 20 according to the present embodiment. In the interpretation WS 3, a viewing request for a medical image to the image server 5, various image processing for the medical image received from the image server 5, display of the medical image, input reception of comments on findings regarding the medical image, and the like are performed. In the interpretation WS 3, an analysis process for medical images and input comments on findings, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6. In the present embodiment, it is assumed that a diagnostic guideline according to the disease is also saved in the image server 5, but the present disclosure is not limited thereto.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, information for accessing a medical image including a specific region, and property information.

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

In the present embodiment, it is assumed that the medical image is a three-dimensional CT image consisting of a plurality of tomographic images with a lung as a diagnosis target, and an interpretation report on an abnormal shadow included in the lung is created by interpreting the CT image in the interpretation WS 3. The medical image is not limited to the CT image, and any medical image such as an MM image and a simple two-dimensional image acquired by a simple X-ray imaging apparatus can be used.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
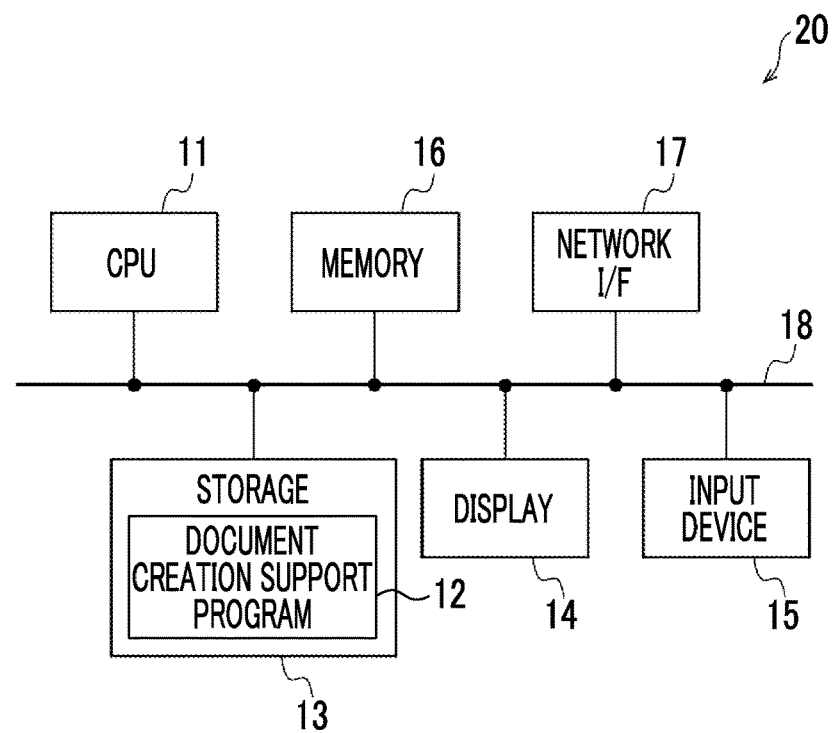
FIG. 2 is a diagram showing a schematic configuration of the document creation support apparatus according to the first embodiment.

Next, the document creation support apparatus according to a first embodiment of the present disclosure will be described. FIG. 2 illustrates a hardware configuration of the document creation support apparatus according to the first embodiment. As shown in FIG. 2, the document creation support apparatus 20 includes a central processing unit (CPU) 11, a non-volatile storage 13, and a memory 16 as a temporary storage area. Further, the document creation support apparatus 20 includes a display 14 such as a liquid crystal display, an input device 15 such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. A document creation support program 12 is stored in the storage 13 as a storage medium. The CPU 11 reads a document creation support program from the storage 13, loads the read document creation support program 12 into the memory 16, and executes the loaded document creation support program 12.

Figure 3:
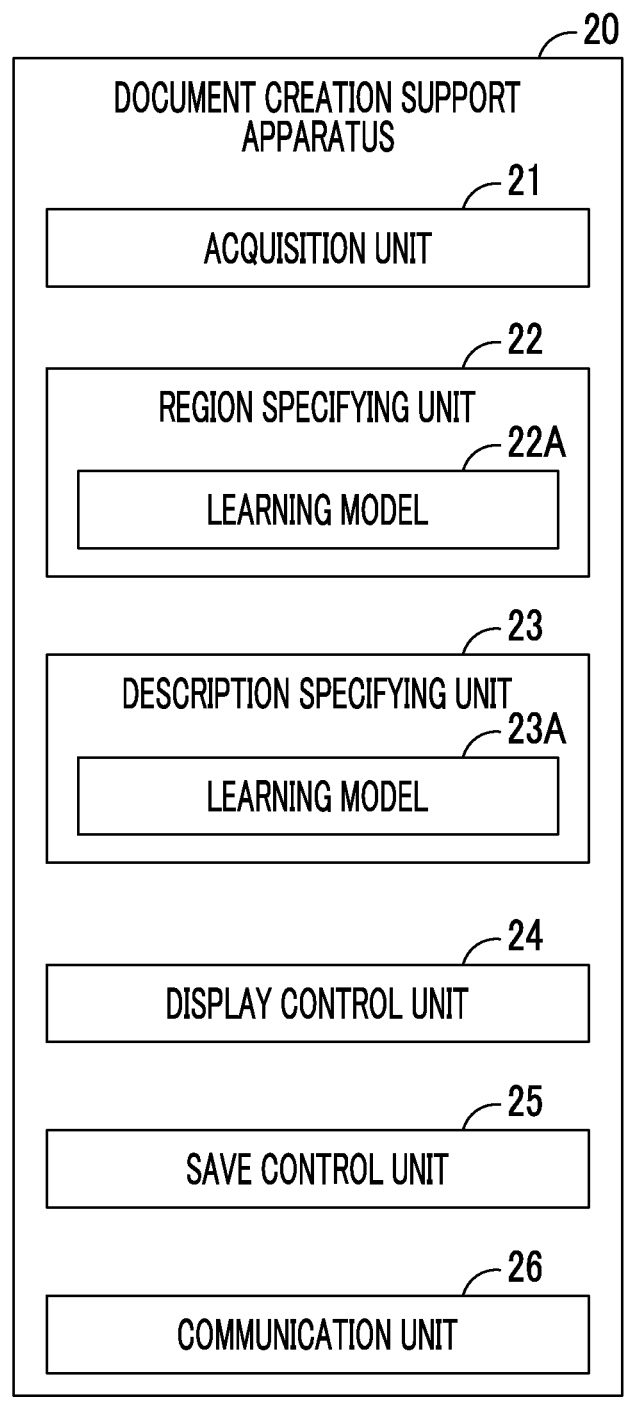
FIG. 3 is a functional configuration diagram of the document creation support apparatus according to the first embodiment.

Next, a functional configuration of the document creation support apparatus according to the first embodiment will be described. FIG. 3 is a diagram showing a functional configuration of the document creation support apparatus according to the first embodiment. As shown in FIG. 3, the document creation support apparatus 20 according to the first embodiment comprises an acquisition unit 21, a region specifying unit 22, a description specifying unit 23, a display control unit 24, a save control unit 25, and a communication unit 26. Then, in a case where the CPU 11 executes the document creation support program, the CPU 11 functions as the acquisition unit 21, the region specifying unit 22, the description specifying unit 23, the display control unit 24, the save control unit 25, and the communication unit 26.

The acquisition unit 21 acquires a first medical image G1 for creating an interpretation report from the image server 5 according to an instruction from the input device 15 by the radiologist who is an operator. Further, the acquisition unit 21 acquires, from the image server 5, a plurality of second medical images G2-$i$ ($i$=2 to n, n is the number of second medical images, and the larger n is, the older the imaging time is) whose imaging time is earlier than that of the first medical image G1 for a patient who has acquired the first medical image G1. Further, the acquisition unit 21 acquires an interpretation report R2-$i$ for the plurality of second medical images G2-$i$ from the report server 7. The acquired first medical image G1 and second medical images G2-$i$, and the interpretation report R2-$i$ are saved in the storage 13.

The region specifying unit 22 specifies, with respect to a first region specified in the first medical image G1 of a subject, a second region corresponding to the first region in each of the plurality of second medical images. To this end, the region specifying unit 22 has a learning model 22A that has been trained to detect abnormal shadows on the lungs included in the medical image.

The learning model 22A consists of, for example, a convolutional neural network (CNN) in which deep learning has been performed using supervised training data so as to discriminate whether or not each pixel (voxel) in a medical image represents an abnormal shadow.

The learning model 22A is constructed by machine learning using, for example, a combination of a medical image including an abnormal shadow and correct answer data representing a position of the abnormal shadow in the medical image as supervised training data. In a case where the medical image is input, the learning model 22A outputs a score indicating that each pixel is an abnormal shadow in the input medical image. The score is a score indicating a prominence of abnormal shadows in medical images. The score takes a value of 0 or more and 1 or less, for example, and the larger the value of the score, the higher the likelihood of the abnormal shadow. Then, the learning model 22A extracts pixels having a score equal to or larger than a predetermined threshold value (for example, 0.5) as pixels of abnormal shadows.

The region specifying unit 22 specifies the region of the abnormal shadow in the first medical image G1 as a first region A1 by using the learning model 22A. Although a plurality of abnormal shadows may be specified, it is assumed here that one first region A1 is specified in the first medical image G1 for the sake of description.

The region specifying unit 22 specifies a second region A2-$i$ corresponding to the first region A1 specified in the first medical image G1 in each of the plurality of second medical images G2-$i$. At this time, the region specifying unit 22 may specify the second region A2-$i$ by using the learning model 22A for each of the plurality of medical images G2-$i$. Further, for the second medical image G2-$i$, the abnormal shadow has already been specified, and the information indicating the position of the specified abnormal shadow may be saved in the image server 5 together with the second medical image G2-$i$. In such a case, the acquisition unit 21 may acquire information indicating the position of the abnormal shadow together with the second medical image G2-$i$, and use the information to specify the second region A2-$i$ in the second medical image G2-$i$.

FIG. 4 is a diagram showing a region specified in a medical image. As shown in FIG. 4, in the first medical image G1, the first region A1 is specified. Further, in two second medical images G2-1 and G2-2, second regions A2-1 and A2-2 are specified, respectively. As shown in FIG. 4, in the first medical image G1 and the second medical images G2-1 and G2-2, the newer the imaging time, the larger the specified region.

The description specifying unit 23 specifies a second description regarding the specified second region A2-$i$ in a plurality of sentences related to each of the plurality of second medical images G2-$i$. In the present embodiment, the interpretation report R2-$i$ is created for each of the plurality of second medical images G2-$i$, and is acquired by the acquisition unit 21 and is saved in the storage 13. The description specifying unit 23 specifies the second description regarding the second region A2-$i$ among a plurality of descriptions included in the corresponding interpretation report R2-$i$ for each of the plurality of second medical images G2-$i$. To this end, the description specifying unit 23 has a learning model 23A that has been trained to discriminate the properties of the abnormal shadow included in the medical image for each of a plurality of predetermined property items.

Here, examples of the property item specified for the abnormal shadow include the location of the abnormal shadow, the size of the abnormal shadow, the shape of the boundary (clear and irregular), the type of absorption value (solid type and frosted glass type), the presence or absence of spicula, whether it is a tumor or a nodule, the presence or absence of pleural contact, the presence or absence of pleural invagination, the presence or absence of pleural infiltration, the presence or absence of a cavity, and the presence or absence of calcification.

In the present embodiment, the learning model 23A consists of a convolutional neural network in which deep learning is performed using supervised training data so as to discriminate the properties of abnormal shadows in medical images.

The learning model 23A is trained by machine learning using, for example, a plurality of combinations of a medical image including an abnormal shadow and a property label representing the property of the abnormal shadow as supervised training data. In a case where a medical image is input, the learning model 23A outputs a property score derived for each property item in the abnormal shadow included in the medical image. The property score is a score indicating the prominence of the property for each property item. The property score takes a value of 0 or more and 1 or less, for example, and the larger the value of the property score is, the more pronounced the property is.

For example, in a case where the property score for "the presence or absence of spicula", which is one of the property items of an abnormal shadow, is, for example, 0.5 or more, it is specified that the property for "the presence or absence of spicula" of the abnormal shadow is "with spicula (positive)", and in a case where the property score for "the presence or absence of spicula" is less than, for example, 0.5, it is specified that the property for the presence or absence of spicula of the abnormal shadow is "no spicula (negative)". The threshold value 0.5 used for property determination is merely an example, and is set to an appropriate value for each property item.

FIG. 5 is a diagram for describing an example of property information specified by the description specifying unit 23. As shown in FIG. 5, in property information 30 specified by the description specifying unit 23, the properties for each property item are "under left lung pleura", "4.2 cm", "irregular", "solid", "with spicula", "tumor", "with pleural contact", "with pleural invagination", "no pleural infiltration", "no cavity", and "no calcification". In FIG. 5, + is given in the case of "yes", that is, positive, and—is given in the case of "no", that is, negative.

Further, the description specifying unit 23 specifies a second description D2-i regarding the second region A2-i, which is included in the interpretation report R2-i, based on the property information 30 extracted for the second region A2-i.

FIG. 6 is a diagram for describing the specification of the second description. Further, in FIG. 6, the extraction of the second description about one second medical image G2-1 will be described. As shown in FIG. 6, an interpretation report R2-1 for the second medical image G2-1 includes a plurality of descriptions for a plurality of abnormal shadows existing at a plurality of locations. On the other hand, property information 31 about the second region A2-1 included in the second medical image G2-1 is "tumor, with cavity". Therefore, the description specifying unit 23 specifies, in a second description D2-1, the description of "The shadow of the tumor of a right lung S6 is about 6.5×4 cm and is increasing. The cavity in the center of the tumor is also larger than last time" related to the property information 31 among the plurality of descriptions included in the interpretation report R2-i.

In the present embodiment, the plurality of second interpretation reports R2-i for each of the plurality of second medical images G2-i and the plurality of second medical images G2-i have been acquired. Therefore, the description specifying unit 23 specifies the second description D2-i regarding each of the second regions A2-i from each of the plurality of second interpretation reports R2-i. Note that, in one interpretation report R2-i, not only one second description but also a plurality of second descriptions D2-i may be specified.

Further, as the learning model 23A, for example, any learning model such as a support vector machine and a recurrent neural network can be used, in addition to the convolutional neural network.

In addition, the description specifying unit 23 is not limited to the specification of the description by the learning model 23A. The second description D2-i may be specified by searching for the second interpretation report R2-i using the size of the tumor and items included in the diagnostic guideline as keywords.

Figure 7:
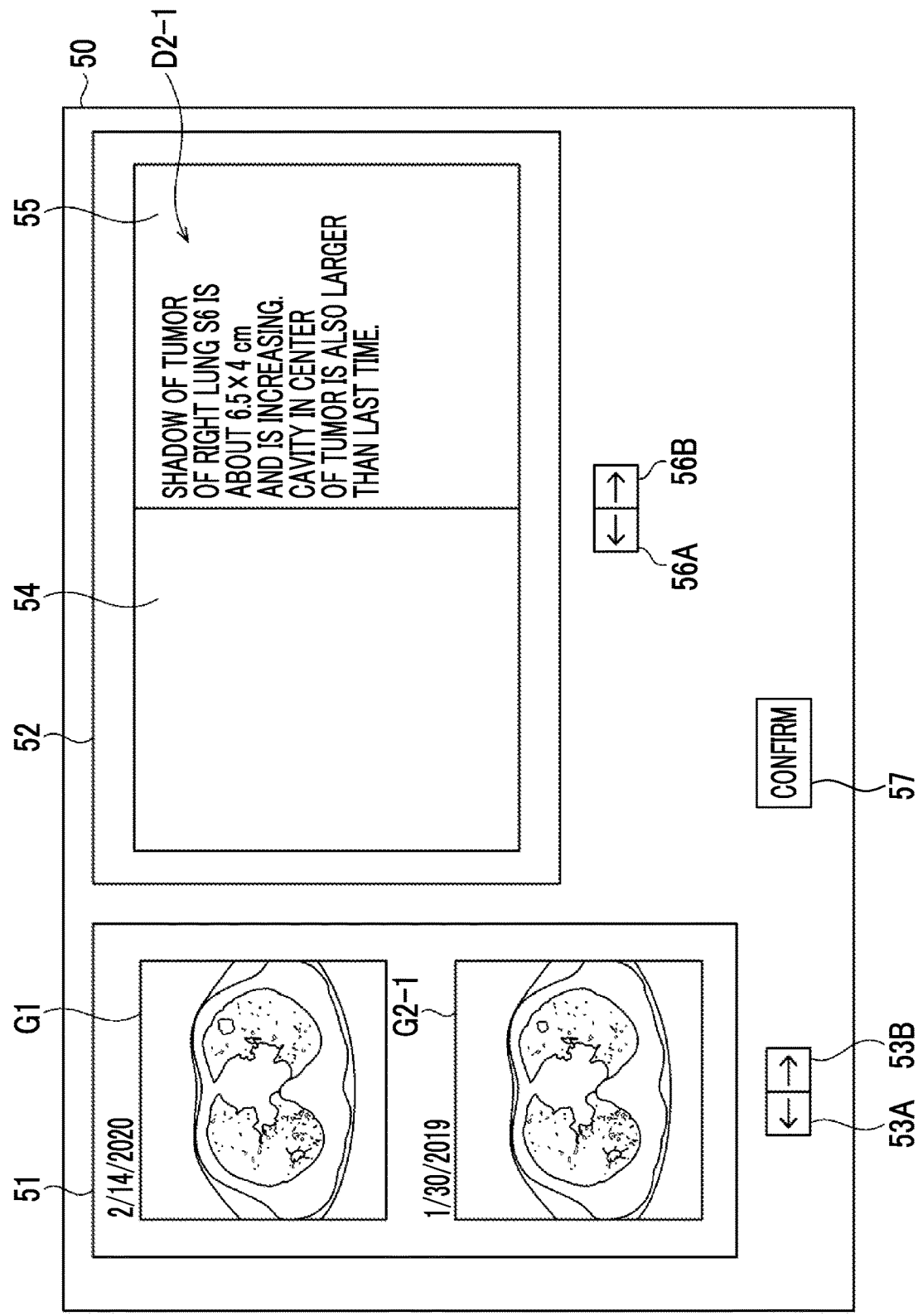
FIG. 7 is a diagram showing a display screen in the first embodiment.

The display control unit 24 displays the plurality of second descriptions D2-i specified for each of the plurality of second medical images G2-i on the display 14 in a switchable manner. FIG. 7 is a diagram showing a display screen in the first embodiment. As shown in FIG. 7, a display screen 50 includes an image display region 51 and a sentence display region 52. The first medical image G1 is displayed in the image display region 51, and the plurality of second medical images G2-i are displayed below the first medical image G1 in a switchable manner. In FIG. 7, the second medical image G2-1 shown in FIG. 4 is displayed. Further, above the first medical image G1 and the second medical images G2-i, the imaging date and time of each medical image is displayed. Below the first medical image G1 and the second medical images G2-i, first switching buttons 53A and 53B for switching the tomographic image displayed for the first medical image G1 are displayed.

The switching display of the second medical images G2-i can be performed by selecting second switching buttons 56A and 56B, which will be described later.

The sentence display region 52 has a first description region 54 for describing an interpretation report for the first medical image G1, and a second description region 55 for displaying the second descriptions D2-i about the second medical images G2-i displayed in the image display region 51. In the second description region 55, the second descriptions D2-i about the second medical images G2-i are displayed in a switchable manner. In addition, in FIG. 7, the second description D2-1 about the second medical image G2-1 is displayed in the second description region 55.

The switching display of the second descriptions D2-i can be performed by selecting the switching buttons 56A and 56B displayed below the sentence display region 52. Further, in conjunction with this, the second medical images G2-i displayed in the image display region 51 are also switched. That is, by selecting the left-facing switching button 56A, the imaging date and time of the second medical images G2-i displayed in the image display region 51 becomes new, and the second descriptions D2-i displayed in the second description region 55 correspond to the displayed second medical images G2-i. Further, by selecting the right-facing switching button 56B, the imaging date and time of the second medical images G2-i displayed in the image display region 51 becomes old, and the second descriptions D2-i displayed in the second description region 55 correspond to the displayed second medical images G2-i.

Figure 8:
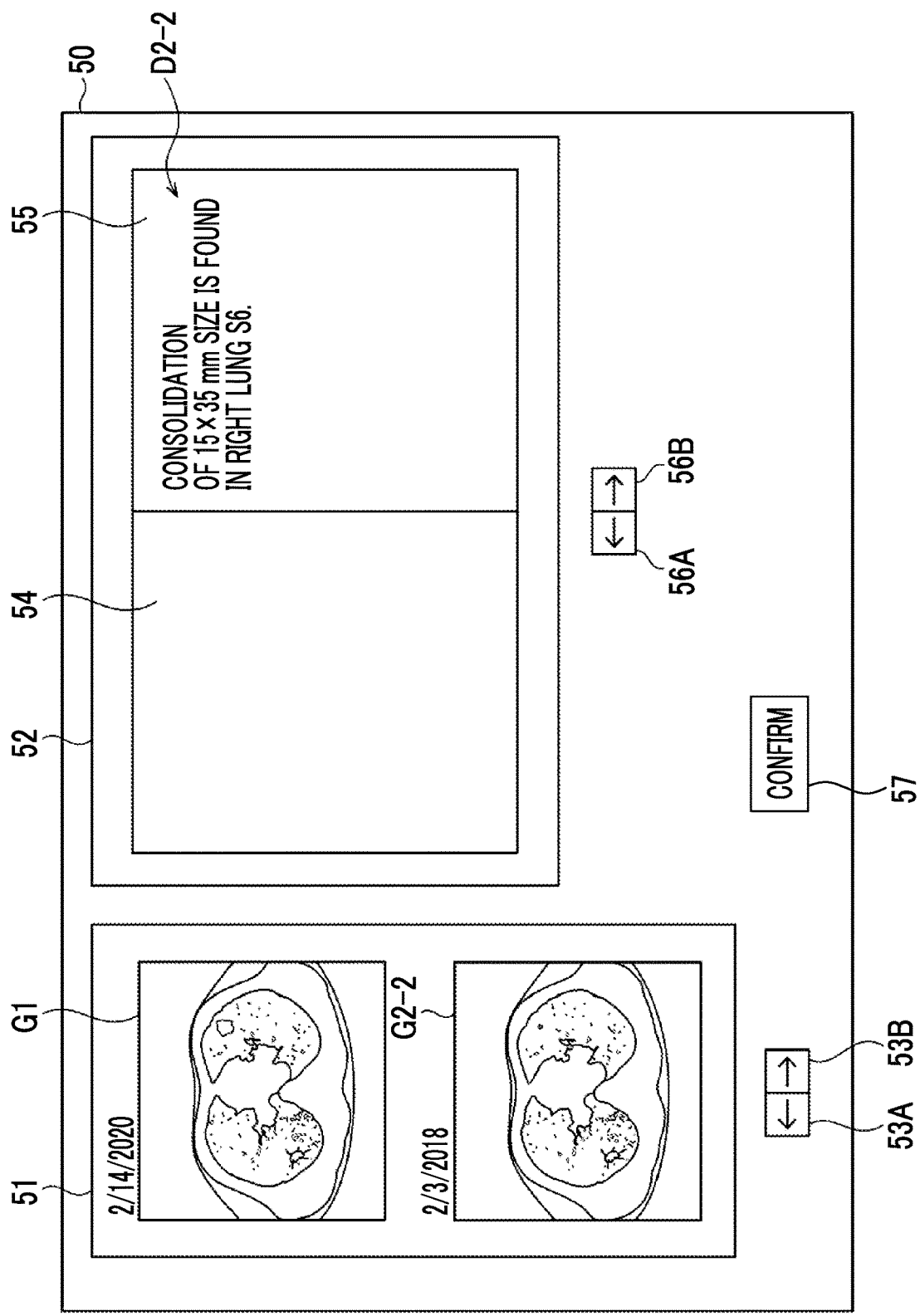
FIG. 8 is a diagram showing a display screen in the first embodiment.

FIG. 8 is a diagram showing a display screen to which the second description has been switched. As shown in FIG. 8, in the second description region 55, a second description D2-2 is displayed in place of the second description D2-1, and in the region below the image display region 51, the second medical image G2-2 is displayed in place of the second medical image G2-1.

In the initial state, it is assumed that the second medical image G2-1 having the latest imaging date and time and the second description D2-1 about the second medical image G2-1 are displayed.

The radiologist refers to the second medical images G2-i displayed in the image display region 51 and the second descriptions D2-i displayed in the sentence display region 52, and describes the findings about the first medical image G1 in the first description region 54. Then, after describing the findings, the confirmation button 57 is selected.

Figure 9:
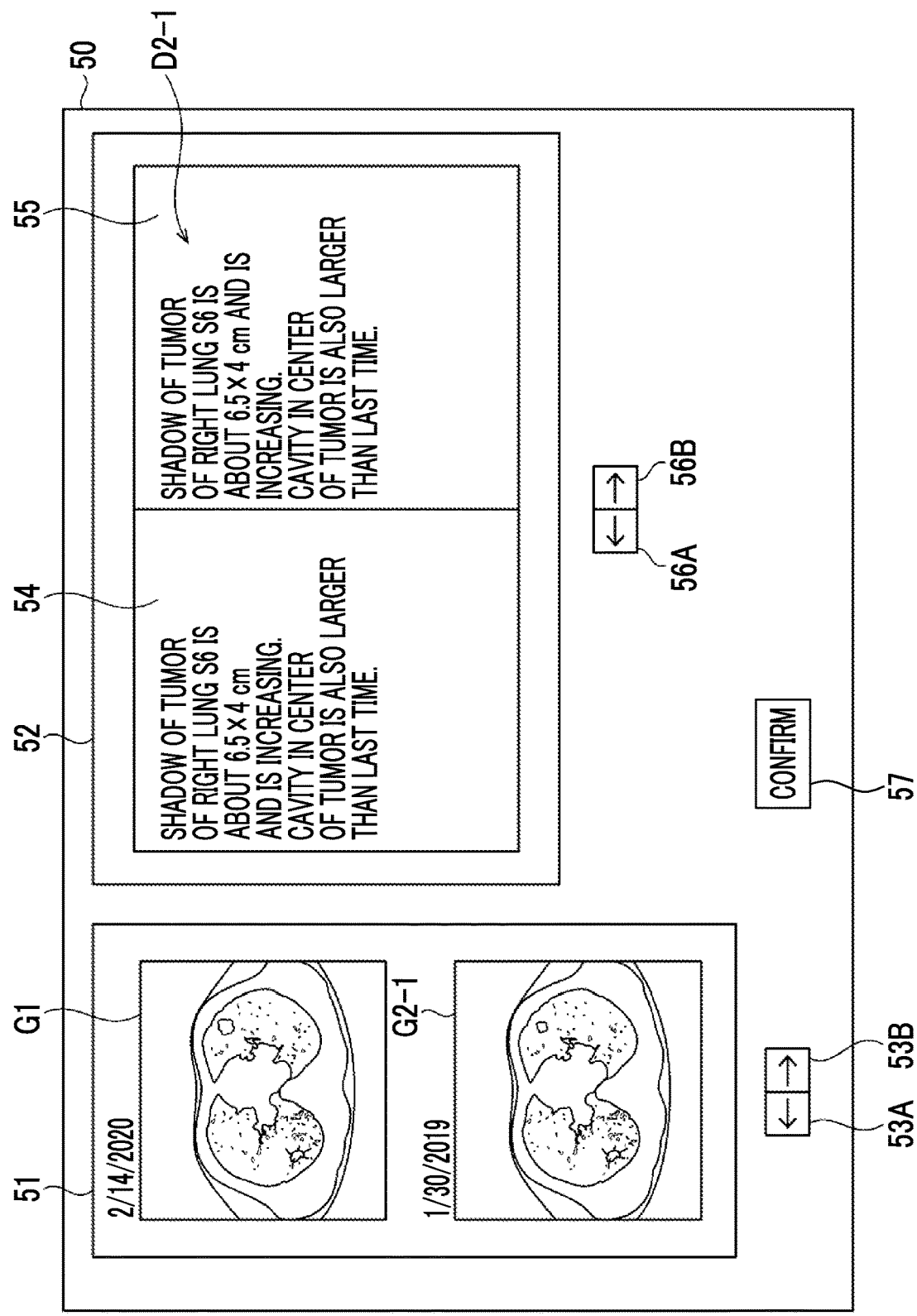
FIG. 9 is a diagram showing a display screen in the first embodiment.

Here, in FIGS. 7 and 8, nothing is described in the first description region 54 in the initial state. However, as shown in FIG. 9, the second description D2-1 about the second medical image G2-1 displayed in the initial state may be transcribed in the first description region 54. In this case, in a case where the displayed second description D2-i is switched and displayed, the description transcribed in the first description region 54 may also be switched. Thereby, in a case where the comments on findings about the first medical image G1 are generated, the second description D2-1 can be easily diverted, and therefore the comments on findings about the first medical image G1 can be easily created.

By the selection of the confirmation button 57 performed by the operator, the save control unit 25 saves the interpretation report including the comments on findings described in the first description region 54 and the first medical image G1 referred to in the case of generating the interpretation report together in the storage 13.

The communication unit 26 transfers the interpretation report including the comments on findings described in the first description region 54 and the first medical image G1 referred to in the case of generating the interpretation report together to the report server 7 via the network I/F 17. The report server 7 saves the interpretation report including the comments on findings described in the first description region 54 and the first medical image G1 referred to in the case of generating the interpretation report together.

Figure 10:
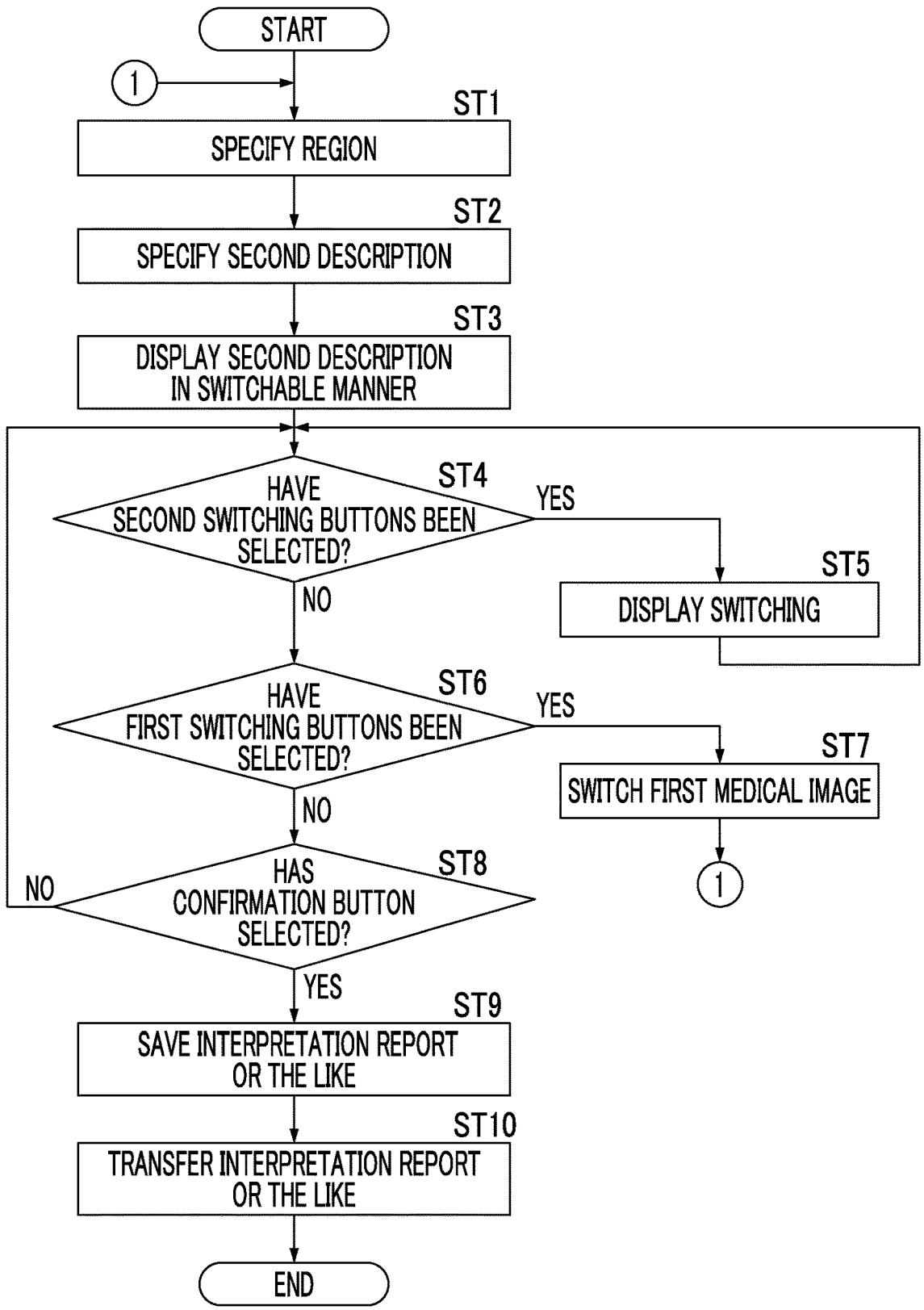
FIG. 10 is a flowchart showing a process performed in the first embodiment.

Next, a process performed in the first embodiment will be described. FIG. 10 is a flowchart showing a process performed in the first embodiment. It is assumed that the first medical image G1 to be interpreted, the plurality of second medical images G2-$i$, and the plurality of interpretation reports R2-$i$ are acquired from the image server 5 and the report server 7 by the acquisition unit 21, and are saved in the storage 13. A process is started in a case where an instruction to create an interpretation report is given by the radiologist, and the region specifying unit 22 specifies the first region A1 and the second region A2-$i$ which are abnormal shadows by analyzing the first medical image G1 and the plurality of second medical images G2-$i$ (region specification; Step ST1).

Next, the description specifying unit 23 specifies the second description D2-$i$ regarding the specified second region A2-$i$ in the second interpretation report R2-$i$ related to each of the plurality of second medical images G2-$i$ (Step ST2).

Then, the display control unit 24 displays the plurality of second descriptions D2-$i$ specified for each of the plurality of second medical images G2-1 on the display 14 in a switchable manner (Step ST3). In this state, the radiologist can describe the comments on findings about the first medical image G1 in the first description region 54.

On the other hand, the display control unit 24 determines whether or not the second switching buttons 56A and 56B have been selected (Step ST4). In a case where Step ST4 is affirmative, the display control unit 24 switches between the second medical images G2-$i$ displayed in the image display region 51 and the second descriptions D2-$i$ displayed in the sentence display region 52 (display switching; Step ST5) and returns to Step ST4. In a case where Step ST4 is negative, the display control unit 24 determines whether or not the first switching buttons 53A and 53B have been selected (Step ST6). In a case where Step ST6 is affirmative, the display control unit 24 switches the tomographic image to be displayed in the image display region 51 for the first medical image G1 (Step ST7), and returns to Step ST1. In a case where Step ST6 is negative, it is determined whether or not the confirmation button 57 has been selected (Step ST8). In a case where Step ST8 is negative, the process returns to Step ST4.

In a case where Step ST8 is affirmative, the save control unit 25 saves the first interpretation report R1 and the first medical image G1 for the first medical image G1 together in the storage 13 (saving the interpretation report or the like; Step ST9). Then, the communication unit 26 transfers the first interpretation report R1 and the first medical image G1 together to the report server 7 via the network I/F 17 (transfer of the interpretation report or the like; Step ST10), and ends the process.

Here, in the case of creating an interpretation report by interpreting the latest medical image of a certain patient, there may be a plurality of interpretation reports (second interpretation reports R2-$i$) for each of a plurality of past medical images (second medical images G2-$i$) for the same patient. In such a case, if the description about the abnormal shadow included in the interpretation report for the past image (that is, the second medical image G2-$i$) can be referred to, the interpretation report including the findings about the abnormal shadow included in the current medical image (that is, the first medical image G1) can be efficiently created.

In the first embodiment, in the case of creating the interpretation report R1 for the first medical image G1, the second descriptions D2-$i$ included in the second interpretation report R2-$i$ for the plurality of medical images G2-$i$ are displayed in a switchable manner. Therefore, in a case where there are a plurality of images of the same patient at different imaging times, the second descriptions D2-$i$ included in the interpretation report R2-$i$ for the past images can be efficiently referred to. Therefore, it is possible to efficiently create the interpretation report R1 for the first medical image G1.

Figure 11:
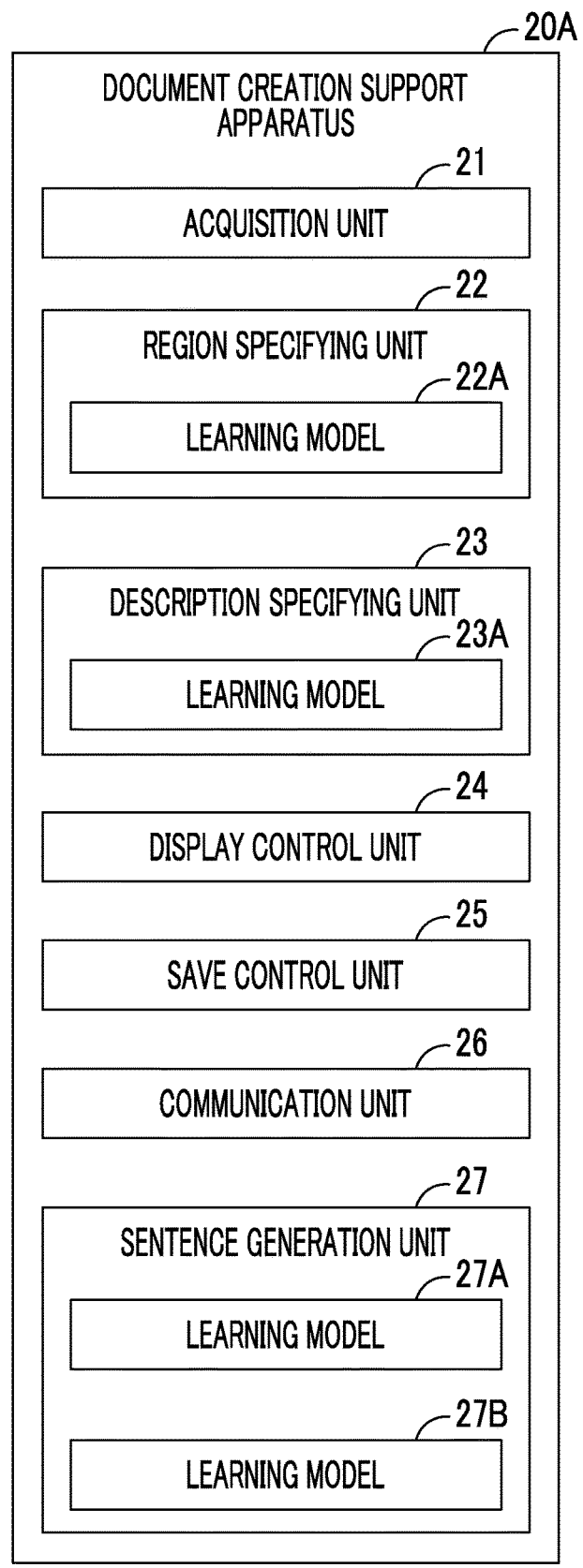
FIG. 11 is a functional configuration diagram of a document creation support apparatus according to a second embodiment.

Next, a second embodiment of the present disclosure will be described. FIG. 11 is a diagram showing a functional configuration of the document creation support apparatus according to the second embodiment. In FIG. 11, the same reference numerals are assigned to the same configurations as those in FIG. 3, and detailed description thereof will be omitted. As shown in FIG. 11, a document creation support apparatus 20A according to the second embodiment is different from the first embodiment in that it further comprises a sentence generation unit 27.

The sentence generation unit 27 analyzes the first region A1 specified by the region specifying unit 22 in the first medical image G1 to generate a first description D1 regarding the first region A1. To this end, the sentence generation unit 27 has a learning model 27A for discriminating the properties of the first region A1 for each of a plurality of predetermined property items. The learning model 27A consists of a convolutional neural network that has been trained in the same manner as the learning model 23A possessed by the description specifying unit 23. In a case where the first region A1 is input, the learning model 27A outputs property information representing the properties of the first region A1.

Figure 12:
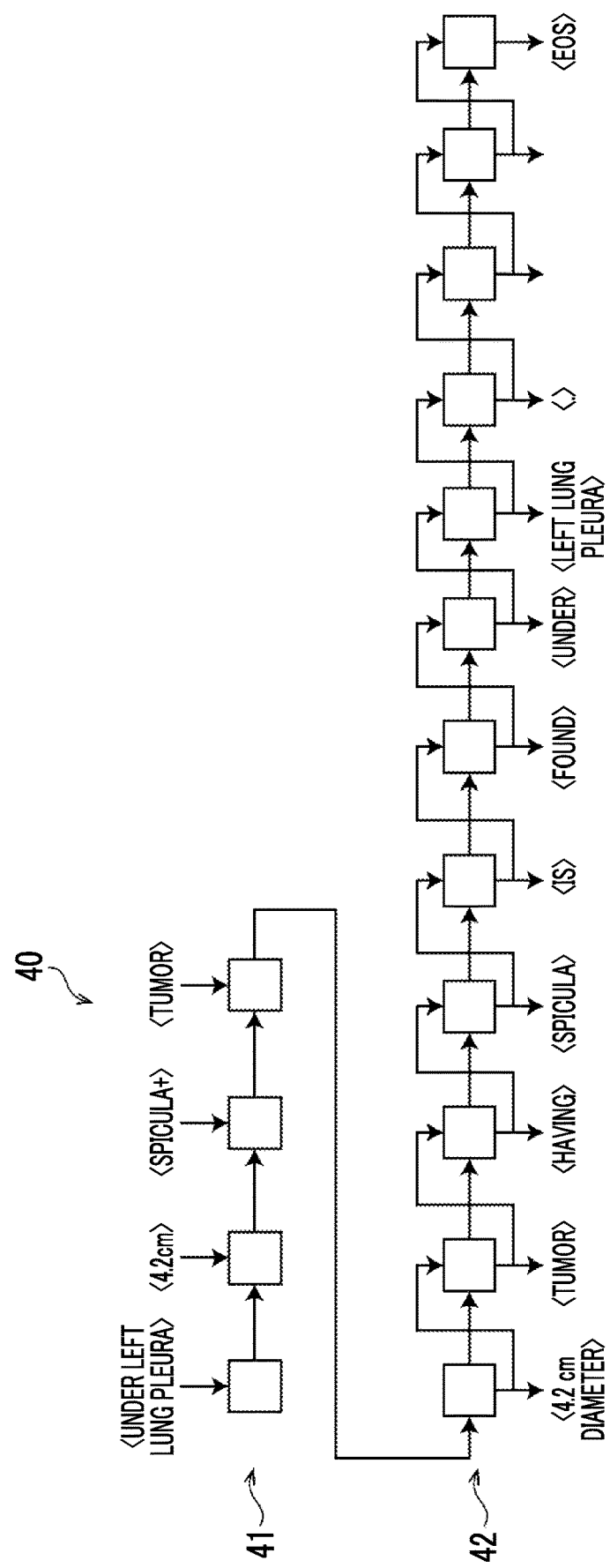
FIG. 12 is a diagram schematically showing a configuration of a recurrent neural network.

In addition, the sentence generation unit 27 generates comments on findings using the derived property information. To this end, the sentence generation unit 27 has a learning model 27B that has been trained to generate a sentence from the input property information. As the learning model 27B, for example, a recurrent neural network can be used. FIG. 12 is a diagram schematically showing a configuration of a recurrent neural network. As shown in FIG. 12, a recurrent neural network 40 consists of an encoder 41 and a decoder 42. The property information output by the learning model 27A is input to the encoder 41. For example, property information indicating "under left lung pleura", "4.2 cm", "spicula+" and "tumor" is input to the encoder 41. The decoder 42 is trained to document character information, and generates a sentence from the input property information. Specifically, from the above-mentioned property information indicating "under left lung pleura", "4.2 cm", "spicula+" and "tumor", a medical sentence "A 4.2 cm diameter tumor having spicula is found under the left lung pleura." is generated. In FIG. 12, "EOS" indicates the end of the sentence (end of sentence).

In this way, in order to output the comments on findings by inputting the property information, the recurrent neural network 40 is constructed by training the encoder 41 and the decoder 42 using a large amount of supervised training data consisting of a combination of the property information and the comments on findings. Note that, the generated sentence shown in FIG. 12 represents the findings about the lung nodule, and is generated by learning the learning model by inputting the property information of the lung nodule.

Figure 13:
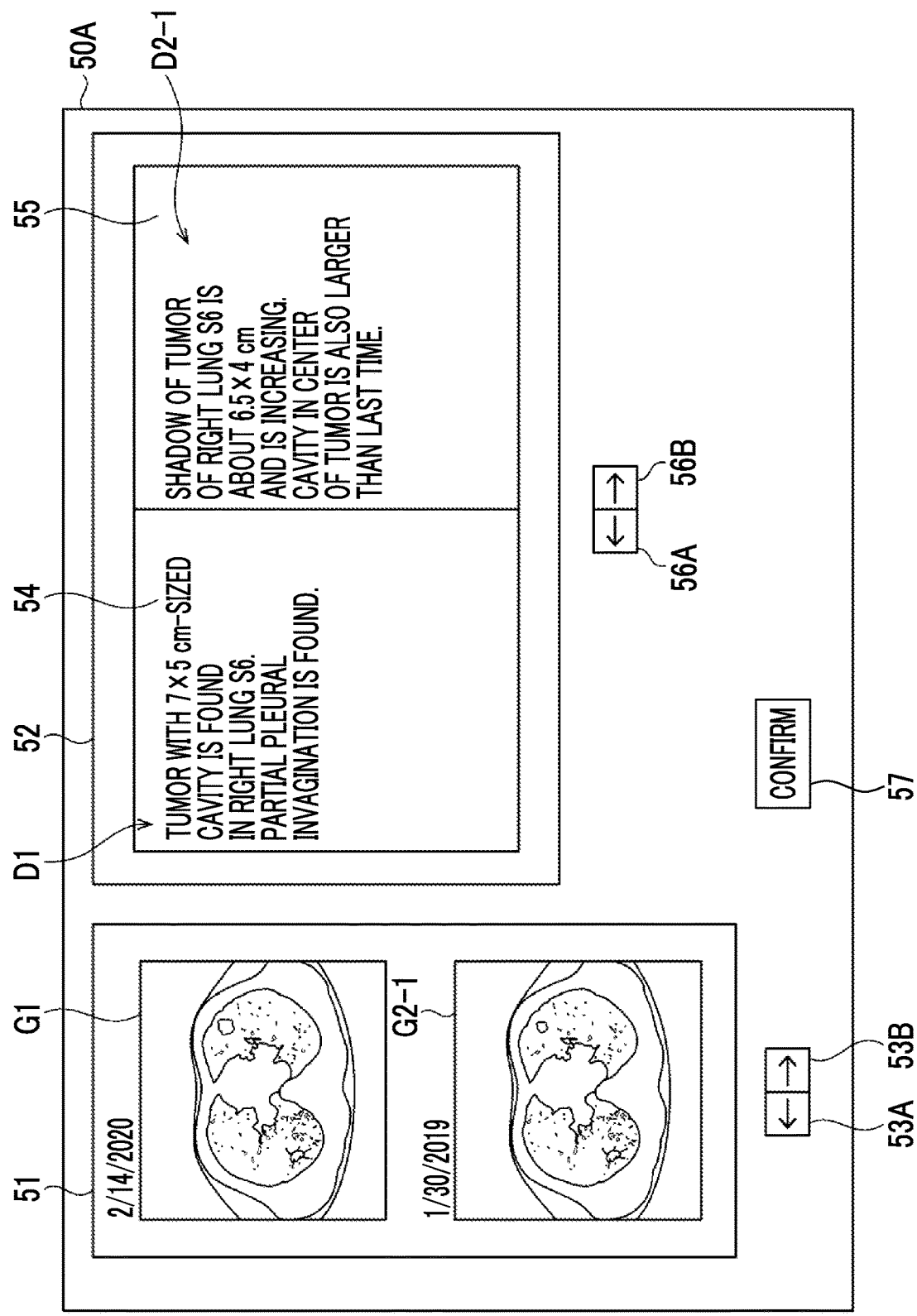
FIG. 13 is a diagram showing a display screen in the second embodiment.

In the second embodiment, the display control unit 24 displays the sentences generated by the sentence generation unit 27, that is, the comments on findings in the first description region 54. FIG. 13 is a diagram showing a display screen in the second embodiment. In FIG. 13, the same reference numerals are assigned to the same configurations as those in FIG. 7, and detailed description thereof will be omitted. As shown in FIG. 13, on the display screen 50A in the second embodiment, in the initial state, the comments on findings regarding the first region A1 included in the first medical image G1 are displayed in the first description region 54 as the first description D1.

Figure 14:
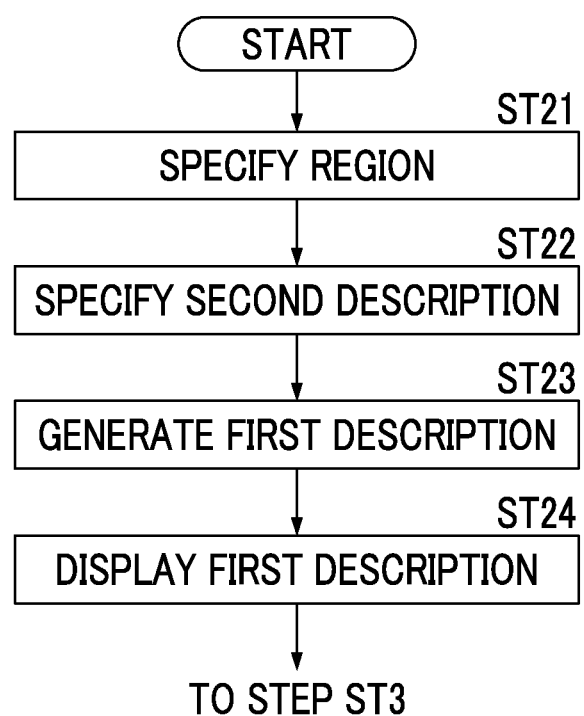
FIG. 14 is a flowchart showing a process performed in the second embodiment.

Next, a process performed in the second embodiment will be described. FIG. 14 is a flowchart showing a process performed in the second embodiment. It is assumed that the first medical image G1 to be interpreted, the plurality of second medical images G2-$i$, and the plurality of interpretation reports R2-$i$ are acquired from the image server 5 and the report server 7 by the acquisition unit 21, and are saved in the storage 13. A process is started in a case where an instruction to create an interpretation report is given by the radiologist, and the region specifying unit 22 specifies the first region A1 and the second region A2-$i$ which are abnormal shadows by analyzing the first medical image G1 and the plurality of second medical images G2-$i$ (region specification; Step ST21).

Next, the description specifying unit 23 specifies the second description D2-$i$ regarding the specified second region A2-$i$ in the second interpretation report R2-$i$ related to each of the plurality of second medical images G2-$i$ (Step ST22). Further, the sentence generation unit 27 generates the first description D1 regarding the first region A1 included in the first medical image G1 (Step ST23). Then, the display control unit 24 displays the first description D1 in the first description region 54 (Step ST24), and proceeds to the process of Step ST3 in FIG. 10. The process of Step ST23 may be performed before the process of Step ST21, or may be performed in parallel with the processes of Steps ST21 and ST22. Further, the process of Step ST24 may be performed after the process of Step ST3 in FIG. 10, or may be performed in parallel with the process of Step ST3.

In this way, in the second embodiment, the first description D1 regarding the first region A1 included in the first medical image G1 is generated, and the first description D1 is displayed in the first description region 54. Therefore, it is possible to reduce the burden on the radiologist who generates the comments on findings about the first region A1 included in the first medical image G1.

In the second embodiment, the first description D1 generated by the sentence generation unit 27 is displayed in the first description region 54, but in addition to the first description D1, the second description D2-$i$ displayed in the second description region 55 may be transcribed in the first description region 54. In this case, in the first description region 54, the first description D1 and the second description D2-$i$ are displayed in a vertically arranged manner, for example.

Figure 15:
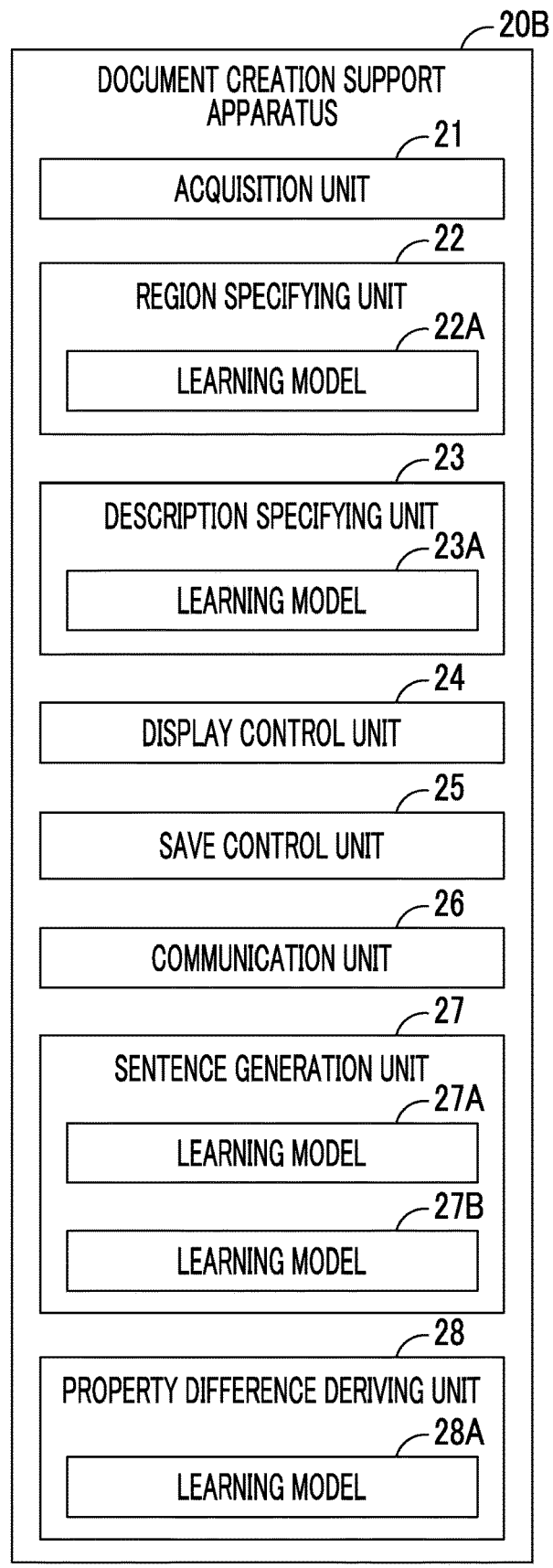
FIG. 15 is a functional configuration diagram of a document creation support apparatus according to a third embodiment.

Next, a third embodiment of the present disclosure will be described. FIG. 15 is a diagram showing a functional configuration of the document creation support apparatus according to the third embodiment. In FIG. 15, the same reference numerals are assigned to the same configurations as those in FIG. 11, and detailed description thereof will be omitted. As shown in FIG. 15, a document creation support apparatus 20B according to the third embodiment is different from the second embodiment in that it further comprises a property difference deriving unit 28.

The property difference deriving unit 28 derives a difference between the properties for the first region A1 included in the first description D1 generated by the sentence generation unit 27 and the properties for the second region A2-$i$ included in the second description D2-$i$ specified for each of the plurality of second medical images G2-$i$. To this end, the property difference deriving unit 28 has a learning model 28A that has been trained to output a difference in properties included in two sentences in a case where the two sentences are input. As the learning model 28A, for example, a recurrent neural network can be used. The recurrent neural network constituting the learning model 28A is constructed by training an encoder and a decoder constituting a recurrent neural network by using a large number of supervised training data consisting of a combination of two sentences and a phrase representing a difference between the two sentences.

Thereby, in a case where, in the learning model 28A of the property difference deriving unit 28, "a tumor with a 7×5 cm-sized cavity is found in a right lung S6. Partial pleural invagination is found" is input as the first description D1 and "A shadow of the tumor of the right lung S6 is about 6.5×4 cm and is increasing. A cavity in the center of the tumor is also larger than last time" is input as the second description D2-$i$, "7×5 cm" and "pleural invagination", which are differences in properties included in the two descriptions, are output.

The property difference deriving unit 28 derives the difference between the property included in the first description D1 and the properties included in all the second descriptions D2-$i$. At this time, the difference between the property included in the first description D1 and the properties included in all the second descriptions D2-$i$ may be derived at once, and each time the second description D2-$i$ is switched and displayed, the difference between the properties included in the displayed second description D2-$i$ and the property included in the first description may be derived. For example, in a case where the switched second description D2-$i$ is "The shadow of the tumor of the right lung S6 is 3×2 cm", the property difference deriving unit 28 outputs "7×5 cm" and "pleural invagination", which are differences between the properties included in the switched second description and the property included in the first description D1.

Figure 16:
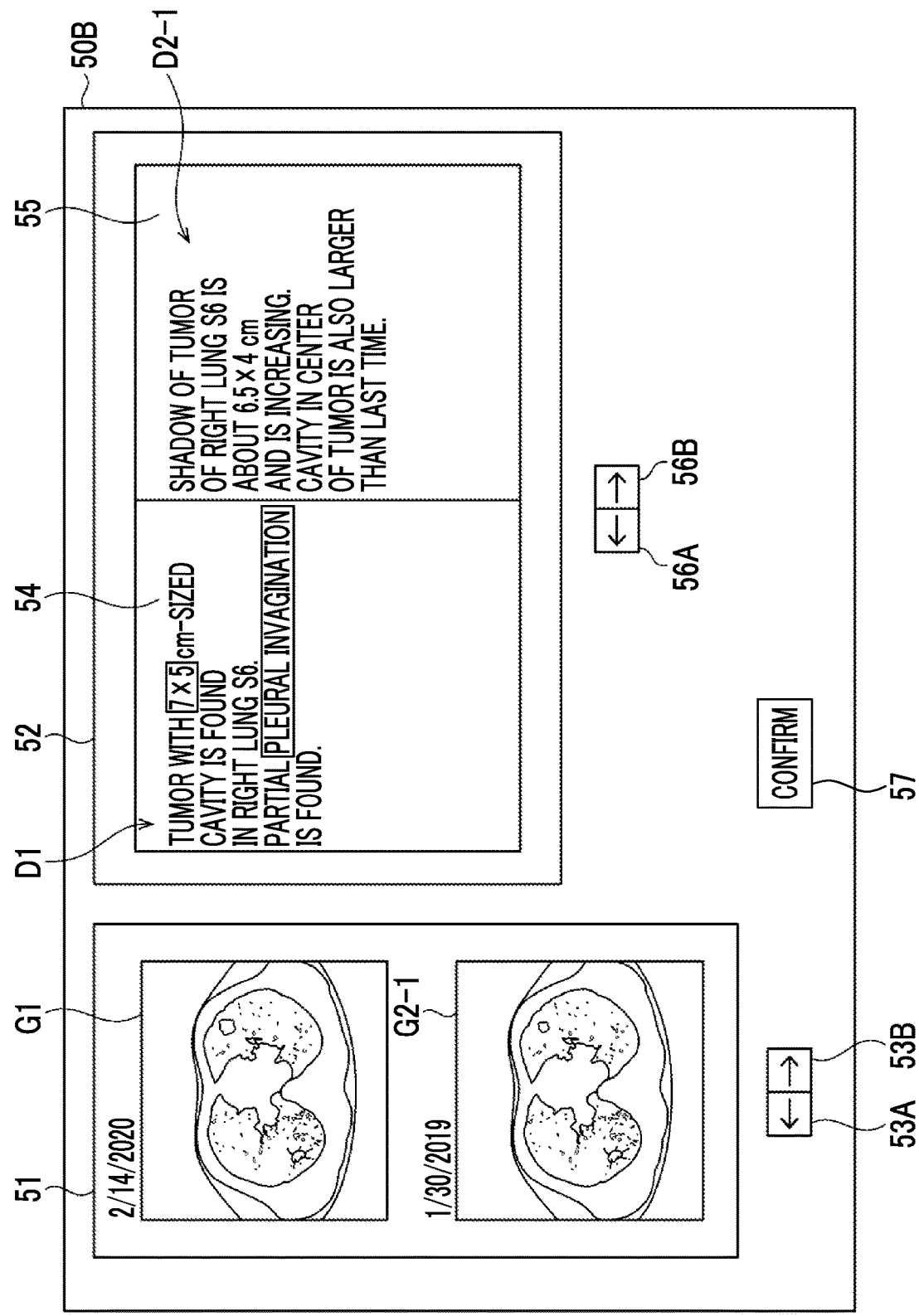
FIG. 16 is a diagram showing a display screen in the third embodiment.

In the third embodiment, in a case where the difference is derived by the property difference deriving unit 28, the display control unit 24 displays the difference between the property included in the first description D1 and the properties included in the second description D2-$i$ on the display 14 in a visually recognizable manner. FIG. 16 is a diagram showing a display screen in the third embodiment. In FIG. 16, the same reference numerals are assigned to the same configurations as those in FIG. 13, and detailed description thereof will be omitted. As shown in FIG. 16, on the display screen 50B in the third embodiment, in the initial state, the first description D1 regarding the first region A1 included in the first medical image G1 is displayed in the first description region 54. Further, in the first description D1, "7×5 cm" and "pleural invagination", which different portions in properties from the displayed second description D2-$i$, are highlighted. In FIG. 16, highlighting is shown by enclosing different properties in a square, but the present disclosure is not limited thereto. Different phrases may be underlined, the background color of different properties may be changed, or the character color of different phrases may be changed.

Figure 17:
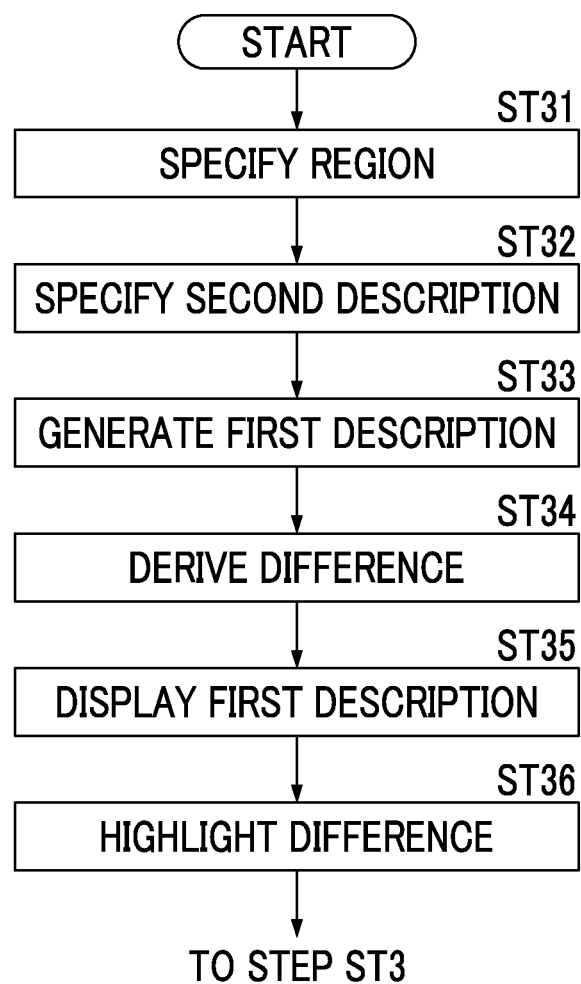
FIG. 17 is a flowchart showing a process performed in the third embodiment.

Next, a process performed in the third embodiment will be described. FIG. 17 is a flowchart showing a process performed in the third embodiment. It is assumed that the first medical image G1 to be interpreted, the plurality of second medical images G2-$i$, and the plurality of interpretation reports R2-$i$ are acquired from the image server 5 and the report server 7 by the acquisition unit 21, and are saved in the storage 13. A process is started in a case where an instruction to create an interpretation report is given by the radiologist, and the region specifying unit 22 specifies the first region A1 and the second region A2-$i$ which are abnormal shadows by analyzing the first medical image G1 and the plurality of second medical images G2-$i$ (region specification; Step ST31).

Next, the description specifying unit 23 specifies the second description D2-$i$ regarding the specified second region A2-$i$ in the second interpretation report R2-$i$ related to each of the plurality of second medical images G2-$i$ (Step ST32). Further, the sentence generation unit 27 generates the first description D1 regarding the first region A1 included in the first medical image G1 (Step ST33). Then, the property difference deriving unit 28 derives the difference between the property included in the first description D1 and the property included in the second description D2-$i$ (Step ST34).

Next, the display control unit 24 displays the first description D1 in the first description region 54 (Step ST35), further highlights the different portion in properties from the second description D2-$i$ in the first description D1 (Step ST36), and proceeds to the process of Step ST3 in FIG. 10. The process of Step ST33 may be performed before the process of Step ST31, or may be performed in parallel with the processes of Steps ST31 and ST32. Further, the processes of Steps ST35 and ST36 may be performed after the process of Step ST3 in FIG. 10, or may be performed in parallel with the process of Step ST3.

In this way, in the third embodiment, the first description D1 regarding the first region A1 included in the first medical image G1 is generated, and the first description D1 is displayed in the first description region 54. Further, at this time, by deriving the differences in properties between the first description D1 and the second description D2-$i$ and highlighting the different portions, the differences in properties can be displayed in a visually recognizable manner. Therefore, it is possible to reduce the burden on the radiologist who generates the comments on findings about the first region A1 included in the first medical image G1, and to check the difference in the description contents regarding the properties of the generated first description D1 and the second description D2-$i$.

In the third embodiment, in the first description D1 the different portions in properties from the second description D2-$i$ are highlighted, but the present disclosure is not limited thereto. In the second description D2-$i$, the different portions from the property of the first description may be highlighted, and the different portions in properties in both the first description D1 and the second description D2-$i$ may be highlighted.

Figure 18:
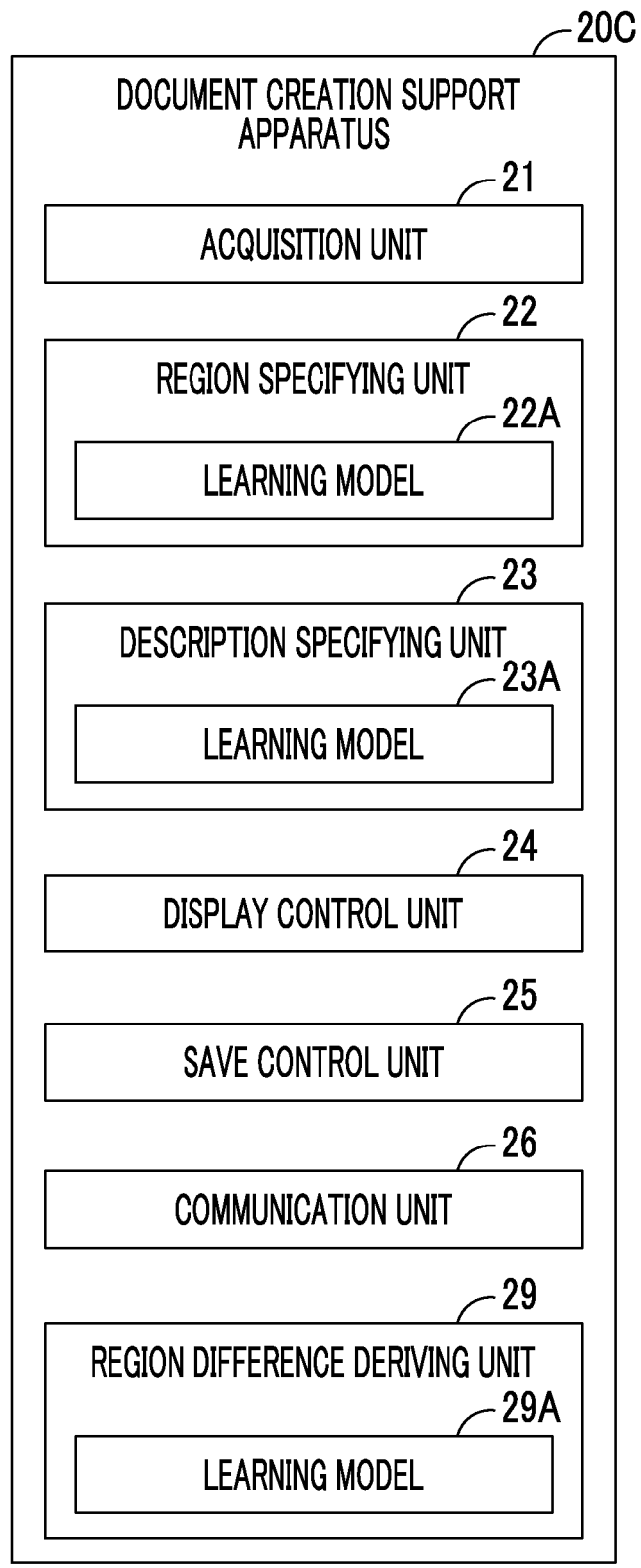
FIG. 18 is a functional configuration diagram of a document creation support apparatus according to a fourth embodiment.

Next, a fourth embodiment of the present disclosure will be described. FIG. 18 is a diagram showing a functional configuration of the document creation support apparatus according to the fourth embodiment. In FIG. 18, the same reference numerals are assigned to the same configurations as those in FIG. 3, and detailed description thereof will be omitted. As shown in FIG. 18, a document creation support apparatus 20C according to the fourth embodiment is different from the first embodiment in that it further comprises a region difference deriving unit 29.

The region difference deriving unit 29 derives a difference between the first region A1 detected from the first medical image G1 and the second region A2-$i$ detected from each of the plurality of second medical images G2-$i$. To this end, the region difference deriving unit 29 has a learning model 29A that has been trained to output a difference between two images in a case where the two images are input. As the learning model 29A, for example, a convolutional neural network can be used. The convolutional neural network constituting the learning model 29A is constructed by training a convolutional neural network by using a large number of supervised training data consisting of a combination of two images and information indicating a difference between the two images (for example, a difference region, a difference value, or the like).

Figure 19:
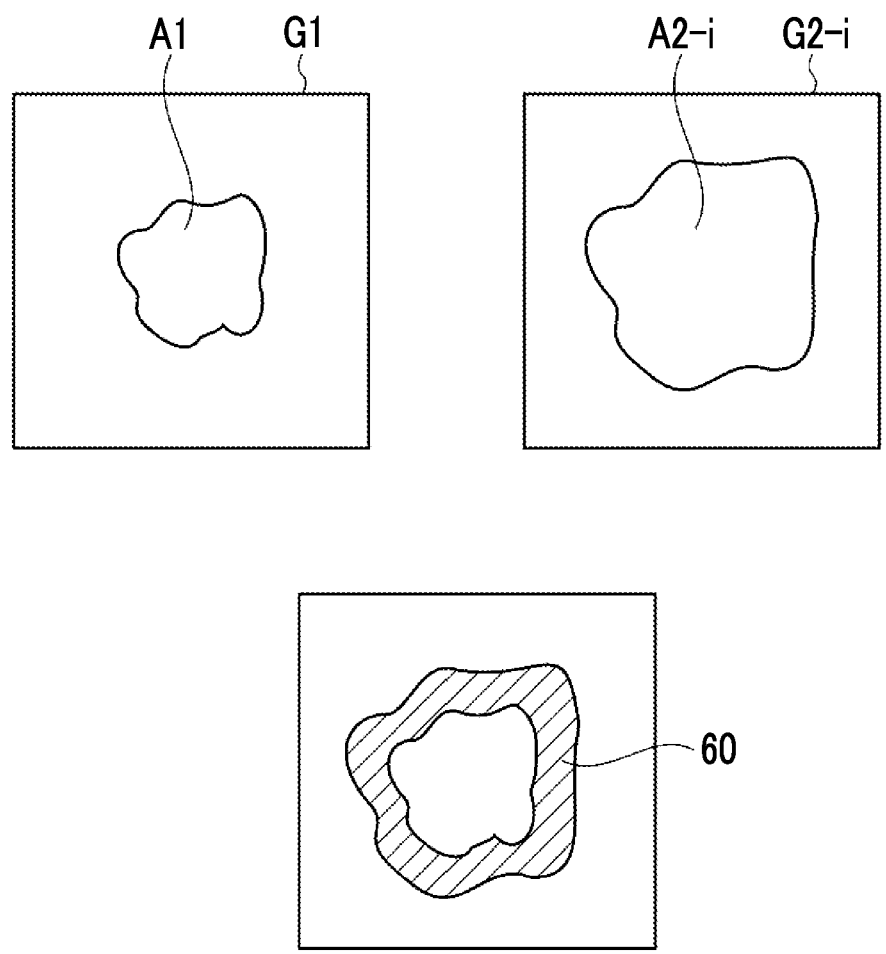
FIG. 19 is a diagram for describing the difference between a first region and a second region.

Thereby, in a case where the first region A1 and the second region A2-$i$ are input to the learning model 29A of the region difference deriving unit 29, the difference between the two regions is output. FIG. 19 is a diagram for describing the derivation of the difference between the two regions. Note that FIG. 19 shows only the abnormal shadows in the first medical image G1 and the second medical image G2-$i$, that is, the partial region including the first region A1 and the second region A2-$i$. As shown in FIG. 19, in a case where the first region A1 in the first medical image G1 is smaller than the second region A2-$i$ in the second medical image G2-$i$, the region difference deriving unit 29 derives a difference 60 in the region as shown in FIG. 19.

The region difference deriving unit 29 derives the difference between the first region A1 and all the second regions A2-$i$. At this time, the difference between the first region A1 and all the second regions A2-$i$ may be derived at once, and each time the second medical image G2-$i$ is switched and displayed, the difference between the second region A2-$i$ and the first region A1 detected from the displayed second medical image G2-$i$ may be derived.

Figure 20:
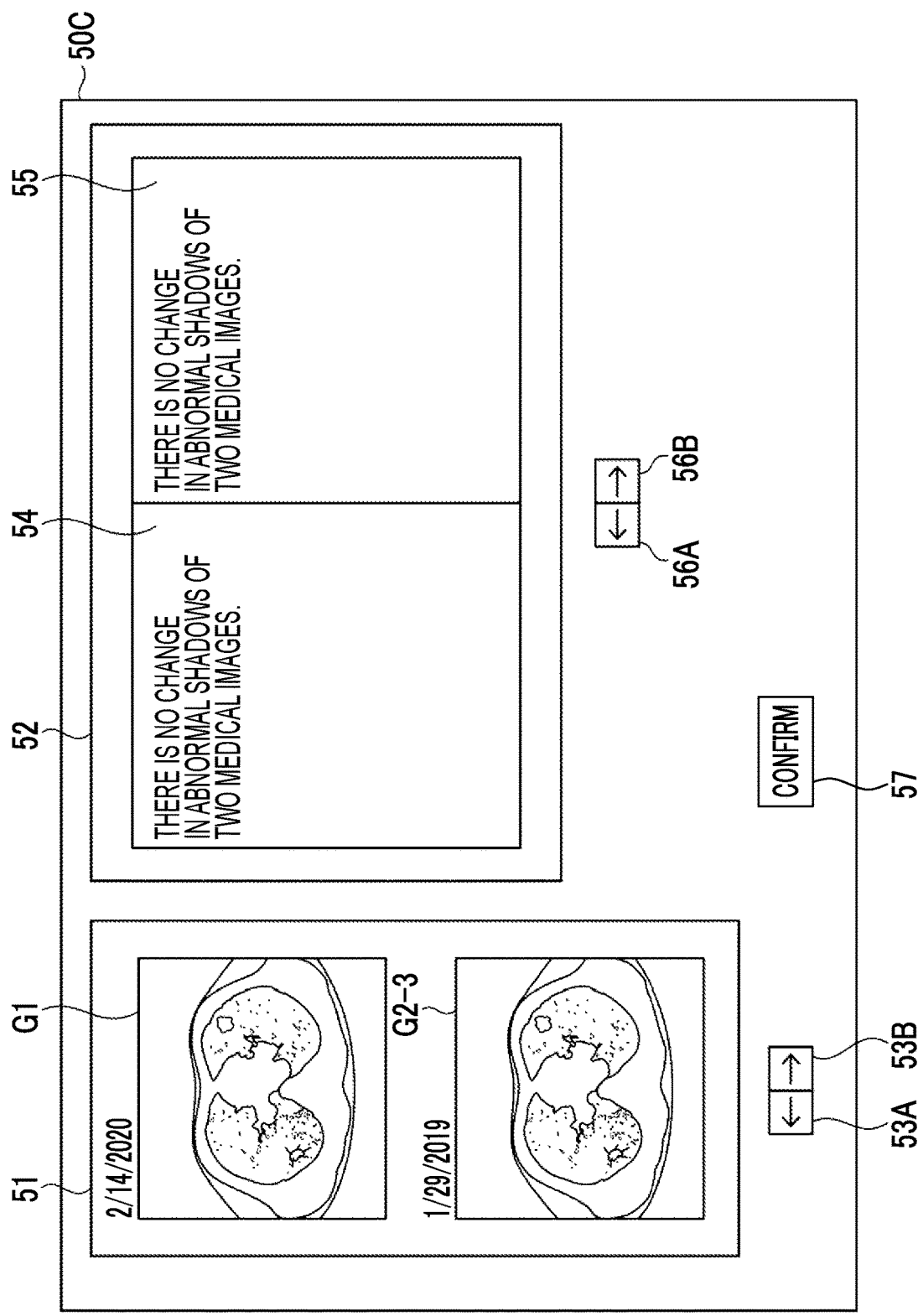
FIG. 20 is a diagram showing a display screen in the fourth embodiment.

In the fourth embodiment, the display control unit 24 displays the second description D2-$i$ in a case where the difference between the first region A1 and the second region A2-$i$ is derived by the region difference deriving unit 29. In addition, in the present embodiment, a plurality of second medical images G2-$i$ are acquired, and regarding the second region A2-$i$ detected from each of the second medical images G2-$i$, there are some that are different from the first region A1 and some that are not different from the first region A1. Therefore, the display control unit 24 displays the second description D2-$i$ in the second description region 55 only in a case where the second medical image G2-$i$ including the second region A2-$i$ that is different from the first region A1 is displayed. On the other hand, in a case where the second medical image G2-$i$ including the second region A2-$i$ that is not different from the first region A1 is displayed, the display control unit 24 displays that there is no difference in the second description region 55. For example, as shown in a display screen 50C of FIG. 20, the display control unit 24 displays, in the image display region 51, a second medical image G2-3 including a second region that is not different from the first region A1 included in the first medical image G1, and displays, in the second description region 55, the text "there is no change in the abnormal shadows of the two medical images".

Figure 21:
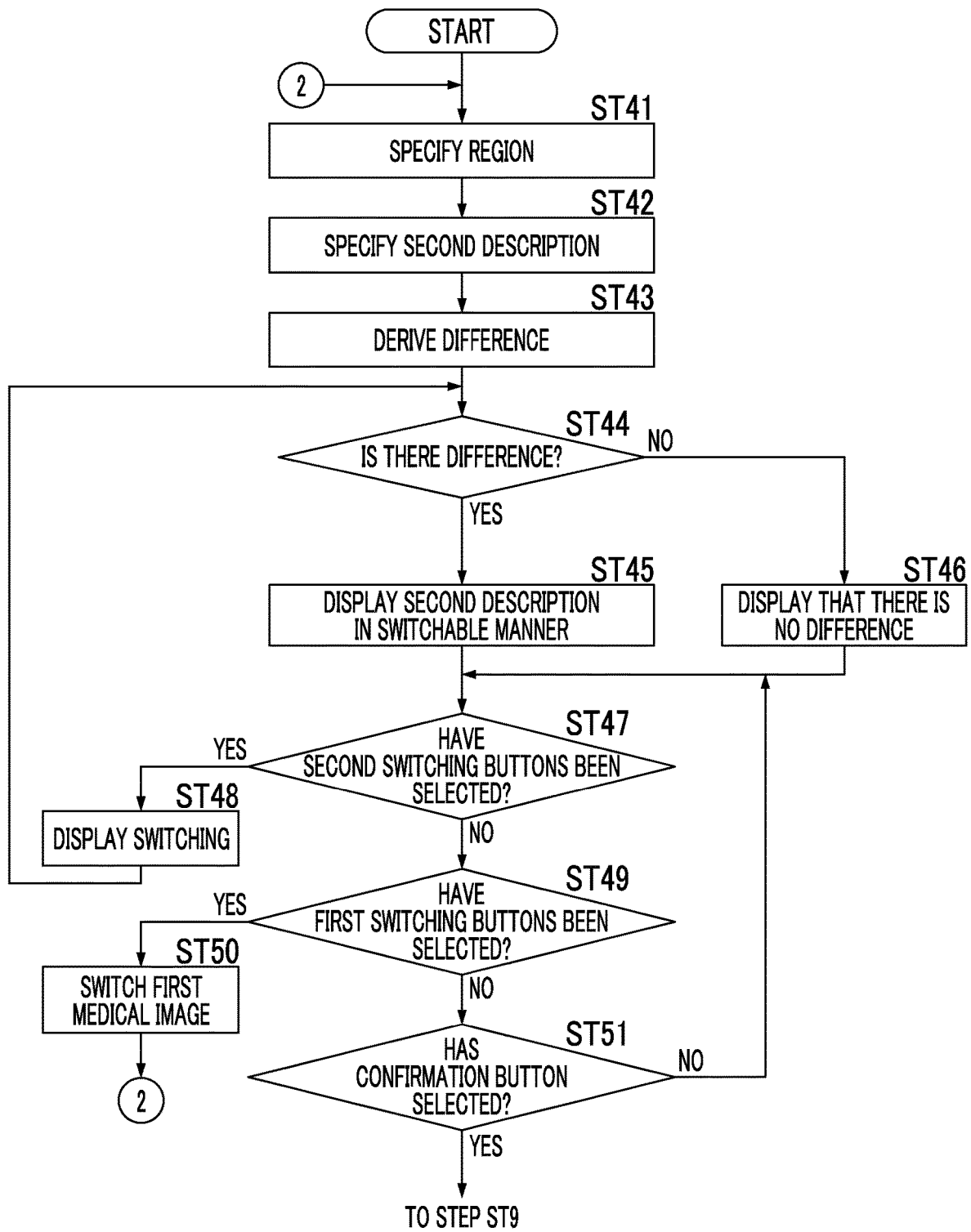
FIG. 21 is a flowchart showing a process performed in the fourth embodiment.

Next, a process performed in the fourth embodiment will be described. FIG. 21 is a flowchart showing a process performed in the fourth embodiment. It is assumed that the first medical image G1 to be interpreted, the plurality of second medical images G2-i, and the plurality of interpretation reports R2-i are acquired from the image server 5 and the report server 7 by the acquisition unit 21, and are saved in the storage 13. A process is started in a case where an instruction to create an interpretation report is given by the radiologist, and the region specifying unit 22 specifies the first region A1 and the second region A2-i which are abnormal shadows by analyzing the first medical image G1 and the plurality of second medical images G2-i (region specification; Step ST41).

Next, the description specifying unit 23 specifies the second description D2-i regarding the specified second region A2-i in the second interpretation report R2-i related to each of the plurality of second medical images G2-i (Step ST42). Further, the region difference deriving unit 29 derives the difference between the first region A1 and the second region A2-i (Step ST43). The process of Step ST43 may be performed before the process of Step ST42, or may be performed in parallel with the process of Step ST42.

Then, the display control unit 24 determines whether or not there is a difference between the first region A1 and the second region A2-i with respect to the second medical image G2-i displayed in the initial state (Step ST44). In a case where Step ST 44 is affirmative, the display control unit 24 displays the second descriptions D2-i specified for the second medical image G2-1 to be displayed in the initial state on the display 14 in a switchable manner (Step ST45). In a case where Step ST44 is negative, the display control unit 24 displays that there is no difference in the second description region 55 (Step ST46).

Following Steps ST45 and ST46, the display control unit 24 determines whether or not the second switching buttons 56A and 56B have been selected (Step ST47). In a case where Step ST47 is affirmative, the display control unit 24 switches the second medical image G2-i to be displayed in the image display region 51 (display switching; Step ST48), and returns to Step ST44. In a case where Step ST47 is negative, the display control unit 24 determines whether or not the first switching buttons 53A and 53B have been selected (Step ST49). In a case where Step ST49 is affirmative, the display control unit 24 switches the tomographic image to be displayed in the image display region 51 for the first medical image G1 (Step ST50), and returns to Step ST41. In a case where Step ST49 is negative, the display control unit 24 determines whether or not the confirmation button 57 has been selected (Step ST51). In a case where Step ST51 is negative, the process returns to Step ST47. In a case where Step ST51 is affirmative, the process proceeds to Step ST9 shown in FIG. 10.

In this way, in the fourth embodiment, the difference between the first region A1 and the second region A2-i is derived, and in a case where there is a difference, the second description D2-i is displayed. Therefore, in a case where there is a change in the abnormal shadow between the first medical image G1 and the second medical image G2-i, the second description D2-i about the abnormal shadow can be referred to. Therefore, with respect to the first medical image G1, it is possible to efficiently create a comment on findings regarding the change in the abnormal shadow.

In the fourth embodiment, in a case where the display control unit 24 displays the second medical image G2-i including the second region A2-i that is not different from the first region A1, the display control unit 24 displays that there is no difference in the second description region 55. However, the present disclosure is not limited thereto. In a case where the second medical image G2-i including the second region A2-i that is not different from the first region A1 is displayed, the display control unit may display the second description D2-i about the second medical image G2-i in the second description region 55, and may display that there is no difference in the first description region 54.

Further, in the fourth embodiment, the region difference deriving unit 29 is provided in the first embodiment, but the present disclosure is not limited thereto. In the second embodiment or the third embodiment, the region difference deriving unit 29 may be provided.

Further, in each of the above embodiments, the technique of the present disclosure is applied in the case of creating an interpretation report using a medical image with the lung as the diagnosis target, but the diagnosis target is not limited to the lung. In addition to the lung, any part of a human body such as a heart, liver, brain, and limbs can be diagnosed. In this case, the diagnostic guideline according to the diagnosis target part may be acquired, and the corresponding portion corresponding to the item of the diagnostic guideline in the interpretation report may be specified.

Further, in each of the above embodiments, for example, as hardware structures of processing units that execute various kinds of processing, such as the acquisition unit 21, the region specifying unit 22, the description specifying unit 23, the display control unit 24, the save control unit 25, the communication unit 26, the sentence generation unit 27, the property difference deriving unit 28, and the region difference deriving unit 29, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. A document creation support apparatus comprising at least one processor,
    wherein the processor is configured to
        specify, with respect to a first region specified in a first image of a subject, a second region corresponding to the first region in each of a plurality of second images of the subject whose imaging time is different from that of the first image,
        specify a second description regarding the specified second region, which is included in a plurality of sentences related to each of the plurality of second images, and
        display each of the plurality of second images along with the corresponding second description in a switchable manner,
    the plurality of second images comprise a first-time second image and a second-time second image respectively imaged at a first imaging time and a second imaging time prior to the imaging time of the first image,
    wherein a first-time second description and a second-time second description are specified for the specified second region respectively in the first-time second image and the second-time second image,
    wherein the processor displays the first-time second image along with the first-time second description in response to the first-time second image or the first-time second description being selected, and
    wherein the processor displays the second-time second image along with the second-time second description in response to the second-time second image or the second-time second description being selected.

2. The document creation support apparatus according to claim 1, wherein the processor is configured to further display a description region for describing a sentence related to the first region.

3. The document creation support apparatus according to claim 2, wherein the processor is configured to transcribe at least one of the plurality of second descriptions to the description region.

4. The document creation support apparatus according to claim 2, wherein the processor is configured to
    analyze the first region to generate a first description regarding the first region, and
    display the first description in the description region.

5. The document creation support apparatus according to claim 4, wherein the processor is configured to
    derive a difference between a property related to the first region included in the first description and a property related to the second region included in the second description specified for each of the plurality of second images, and
    display the difference between the property included in the first description and the property included in the second description in a visually recognizable manner.

6. The document creation support apparatus according to claim 1, wherein the processor is configured to derive a difference between the first region and the second region.

7. The document creation support apparatus according to claim 6, wherein the processor is configured to display the second description in a case where the difference has been derived.

8. The document creation support apparatus according to claim 6, wherein the processor is configured to notify that the difference has not been derived in a case where the difference has not been derived.

9. A document creation support method comprising:
    specifying, with respect to a first region specified in a first image of a subject, a second region corresponding to the first region in each of a plurality of second images of the subject whose imaging time is different from that of the first image;
    specifying a second description regarding the specified second region, which is included in a plurality of sentences related to each of the plurality of second images; and
    displaying each of the plurality of second images along with the corresponding second description in a switchable manner,
    wherein the plurality of second images comprise a first-time second image and a second-time second image respectively imaged at a first imaging time and a second imaging time prior to the imaging time of the first image,
    wherein a first-time second description and a second-time second description are specified for the specified second region respectively in the first-time second image and the second-time second image,
    wherein the first-time second image is displayed along with the first-time second description in response to the first-time second image or the first-time second description being selected, and
    wherein the second-time second image is displayed along with the second-time second description in response to the second-time second image or the second-time second description being selected.

10. A non-transitory computer readable medium storing a document creation support program causing a computer to execute a procedure comprising:
    specifying, with respect to a first region specified in a first image of a subject, a second region corresponding to the first region in each of a plurality of second images of the subject whose imaging time is different from that of the first image;
    specifying a second description regarding the specified second region, which is included in a plurality of sentences related to each of the plurality of second images; and
    displaying each of the plurality of second images along with the corresponding second description in a switchable manner,
    wherein the plurality of second images comprise a first-time second image and a second-time second image respectively imaged at a first imaging time and a second imaging time prior to the imaging time of the first image,
    wherein a first-time second description and a second-time second description are specified for the specified second region respectively in the first-time second image and the second-time second image,
    wherein the first-time second image is displayed along with the first-time second description in response to the first-time second image or the first-time second description being selected, and
    wherein the second-time second image is displayed along with the second-time second description in response to the second-time second image or the second-time second description being selected.

* * * * *